(12) United States Patent
Fisher et al.

(10) Patent No.: US 11,684,777 B2
(45) Date of Patent: Jun. 27, 2023

(54) METHOD AND DEVICE FOR MINIMALLY INVASIVE IN VIVO TRANSFECTION OF ADIPOSE TISSUE USING ELECTROPORATION

(71) Applicant: INOVIO PHARMACEUTICALS, INC., Plymouth Meeting, PA (US)

(72) Inventors: Paul Fisher, Fallbrook, CA (US); Kate Broderick, San Diego, CA (US); Jay McCoy, Temecula, CA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 947 days.

(21) Appl. No.: 16/335,444

(22) PCT Filed: Sep. 22, 2017

(86) PCT No.: PCT/US2017/052970
§ 371 (c)(1),
(2) Date: Mar. 21, 2019

(87) PCT Pub. No.: WO2018/057900
PCT Pub. Date: Mar. 29, 2018

(65) Prior Publication Data
US 2020/0016400 A1    Jan. 16, 2020

Related U.S. Application Data
(60) Provisional application No. 62/480,180, filed on Mar. 31, 2017, provisional application No. 62/398,932, filed on Sep. 23, 2016.

(51) Int. Cl.
*A61N 1/32*     (2006.01)
*A61N 1/04*     (2006.01)

(52) U.S. Cl.
CPC ........... *A61N 1/327* (2013.01); *A61N 1/0416* (2013.01); *A61N 1/0404* (2013.01)

(58) Field of Classification Search
CPC .... A61N 1/327; A61N 1/0412; A61N 1/0416; A61N 1/0424; A61B 2018/00613
See application file for complete search history.

(56) References Cited

U.S. PATENT DOCUMENTS 6,009,345 A     12/1999  Hofmann
6,778,853 B1 *   8/2004  Heller ................... A61M 37/00
                                                         604/20
(Continued)

FOREIGN PATENT DOCUMENTS

DE          10032000 A1     1/2001
JP       2008-302254 A     12/2008
(Continued)

OTHER PUBLICATIONS

Martinez-Lemus et al. "The Dynamic Structure of Arterioles". 2012. Basic Clin Pharmacol Toxicol. Accessed at: https://www.ncbi.nlm.nih.gov/pmc/articles/PMC4435689/ (Year: 2012).*
(Continued)

*Primary Examiner* — Bhisma Mehta
*Assistant Examiner* — John J Crawford
(74) *Attorney, Agent, or Firm* — BakerHostetler

(57) ABSTRACT

A method and device for electroporating adipocytes in the adipose layer of tissue, where the device includes a frame, a first electrode coupled to the frame having a first contact surface, a second electrode coupled to the frame having a second contact surface, and where the first contact surf ace and the second contact surface define a treatment zone therebetween. The method including positioning a fold of tissue between the first and second electrodes such that the
(Continued)

treatment zone formed between the two electrodes includes an adipose layer of tissue and no skeletal muscle.

21 Claims, 26 Drawing Sheets

(56) References Cited

U.S. PATENT DOCUMENTS

| | | | |
|---|---|---|---|
| 2002/0042588 | A1 | 4/2002 | Jaroszeski et al. |
| 2003/0149451 | A1* | 8/2003 | Chomenky ............ A61N 1/327 607/3 |
| 2005/0182462 | A1 | 8/2005 | Chornenky et al. |
| 2005/0182562 | A1 | 8/2005 | Miyazawa |
| 2006/0293725 | A1 | 12/2006 | Rubinsky et al. |
| 2007/0055179 | A1 | 3/2007 | Deem et al. |
| 2007/0060989 | A1 | 3/2007 | Deem et al. |
| 2007/0239075 | A1 | 10/2007 | Rosenberg et al. |
| 2010/0049178 | A1 | 2/2010 | Deem et al. |
| 2011/0009807 | A1 | 1/2011 | Kjeken et al. |
| 2011/0009860 | A1* | 1/2011 | Chornenky ............ A61B 18/14 606/41 |
| 2011/0112520 | A1 | 5/2011 | Michael |
| 2011/0190659 | A1 | 8/2011 | Long et al. |
| 2014/0277219 | A1 | 9/2014 | Nanda |

FOREIGN PATENT DOCUMENTS

| | | |
|---|---|---|
| JP | 2009-506870 A | 2/2009 |
| JP | 2009-506873 A | 2/2009 |
| JP | 2010-524591 A | 7/2010 |
| WO | 2009/091578 A1 | 7/2009 |
| WO | 2015192018 A1 | 12/2015 |

OTHER PUBLICATIONS

Georgescu et al. "Dysfunction of human subcutaneous fat arterioles in obesity alone or obesity associated with Type 2 diabetes". 2011. Clin Sci (Lond). Accessed at: https://pubmed.ncbi.nlm.nih.gov/20979575/ (Year: 2011).*

Grizelj et al. Reduced flow-and acetylcholine-induced dilation in visceral compared to subcutaneous adipose arterioles in human morbid obesity. 2015. Microcirculation. Accessed at: https://www.ncbi.nlm.nih.gov/pmc/articles/PMC4779122/ (Year: 2015).*

International Search Report and Written Opinion issued in PCT/US2017/052970, dated Dec. 5, 2017.

International Preliminary Report on Patentability and Written Opinion issued in PCT/US2017/052970, dated Apr. 4, 2019.

* cited by examiner

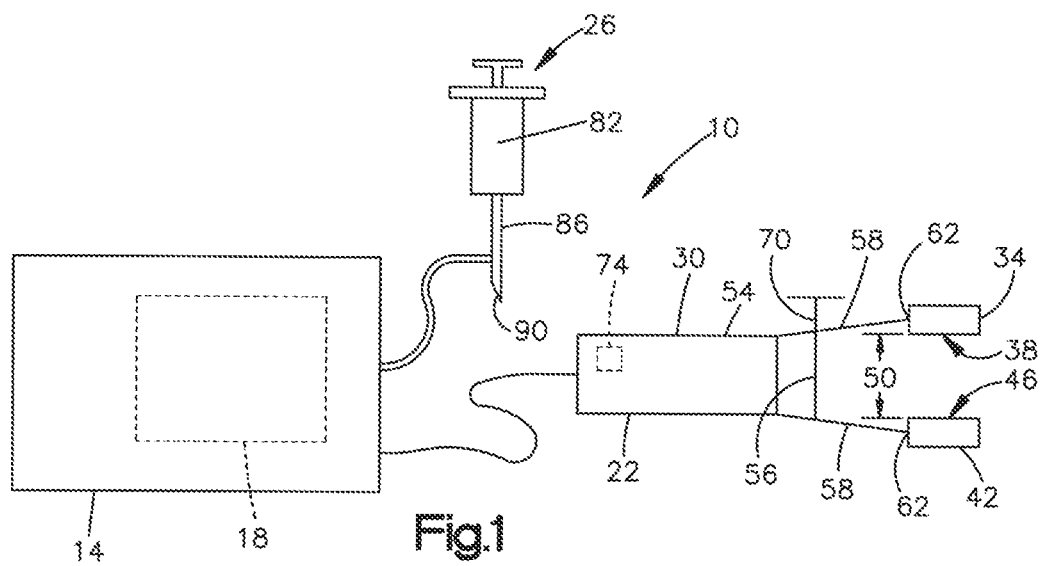
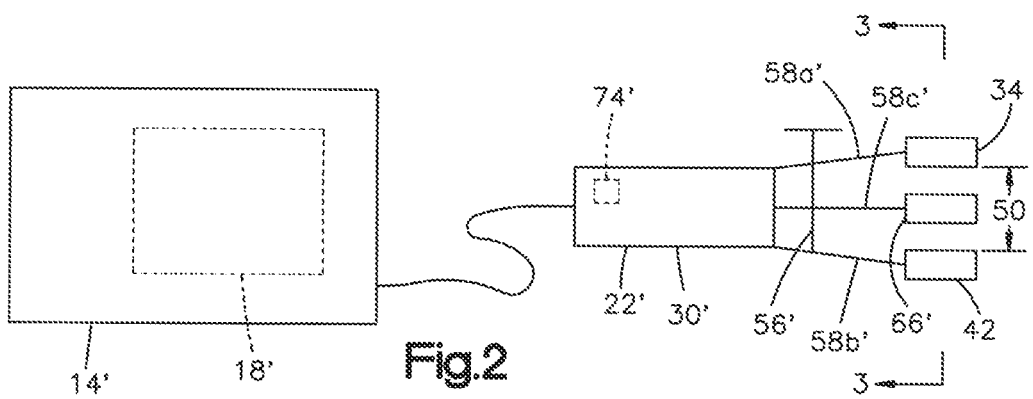
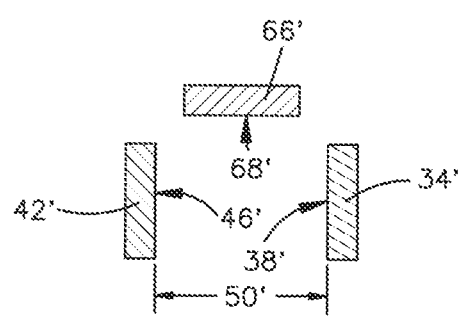

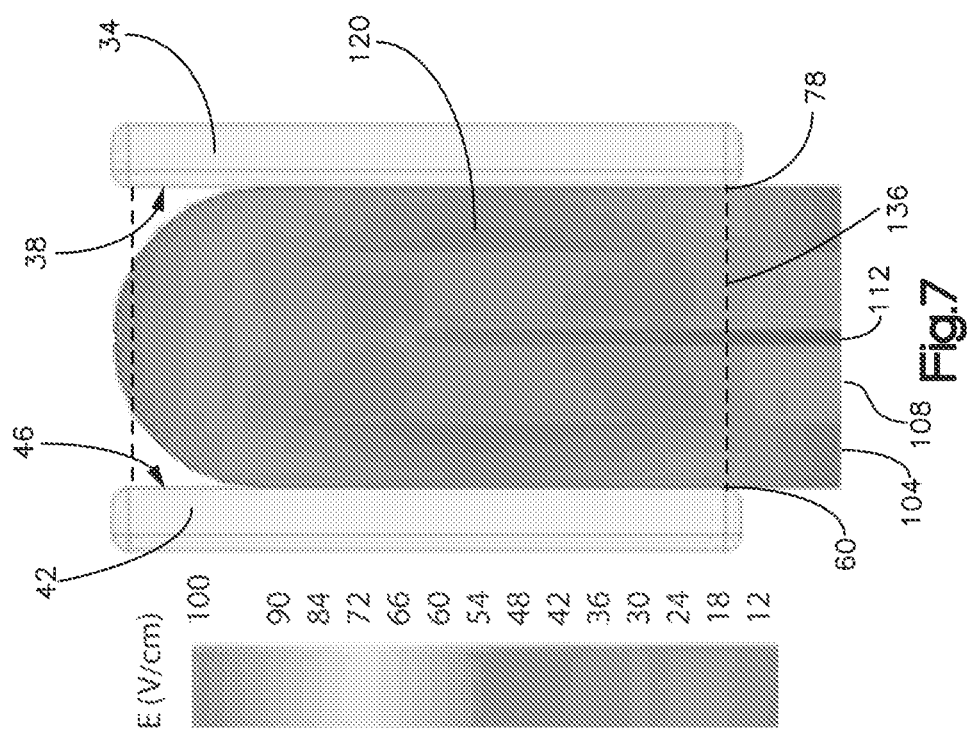
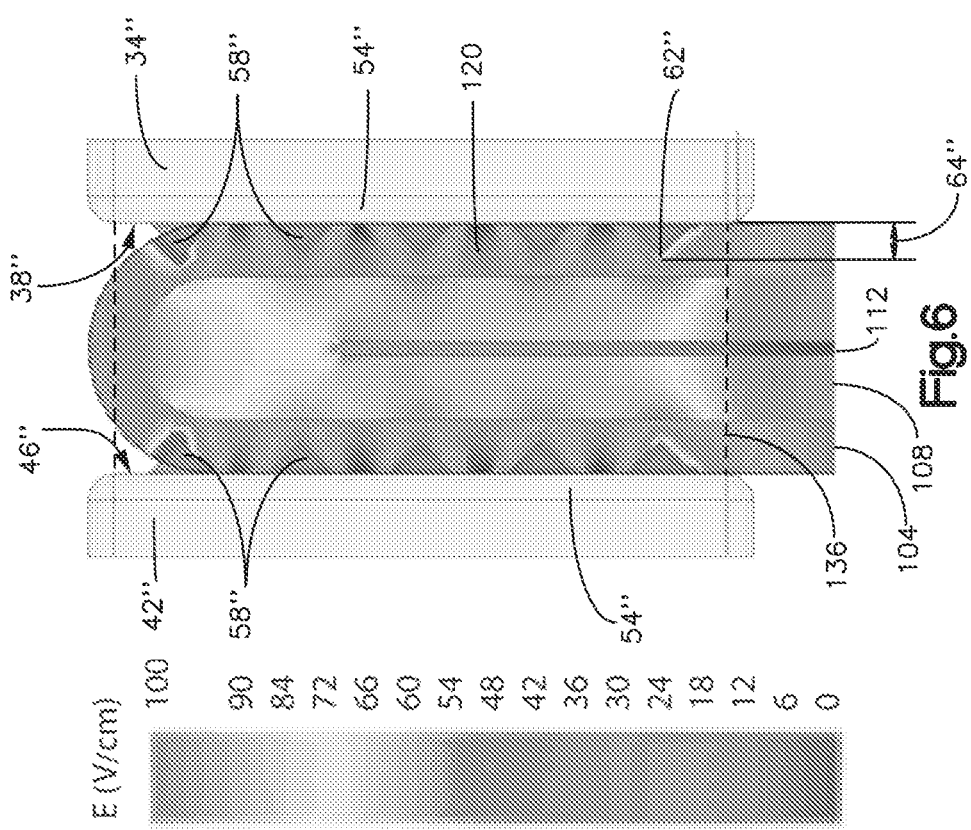

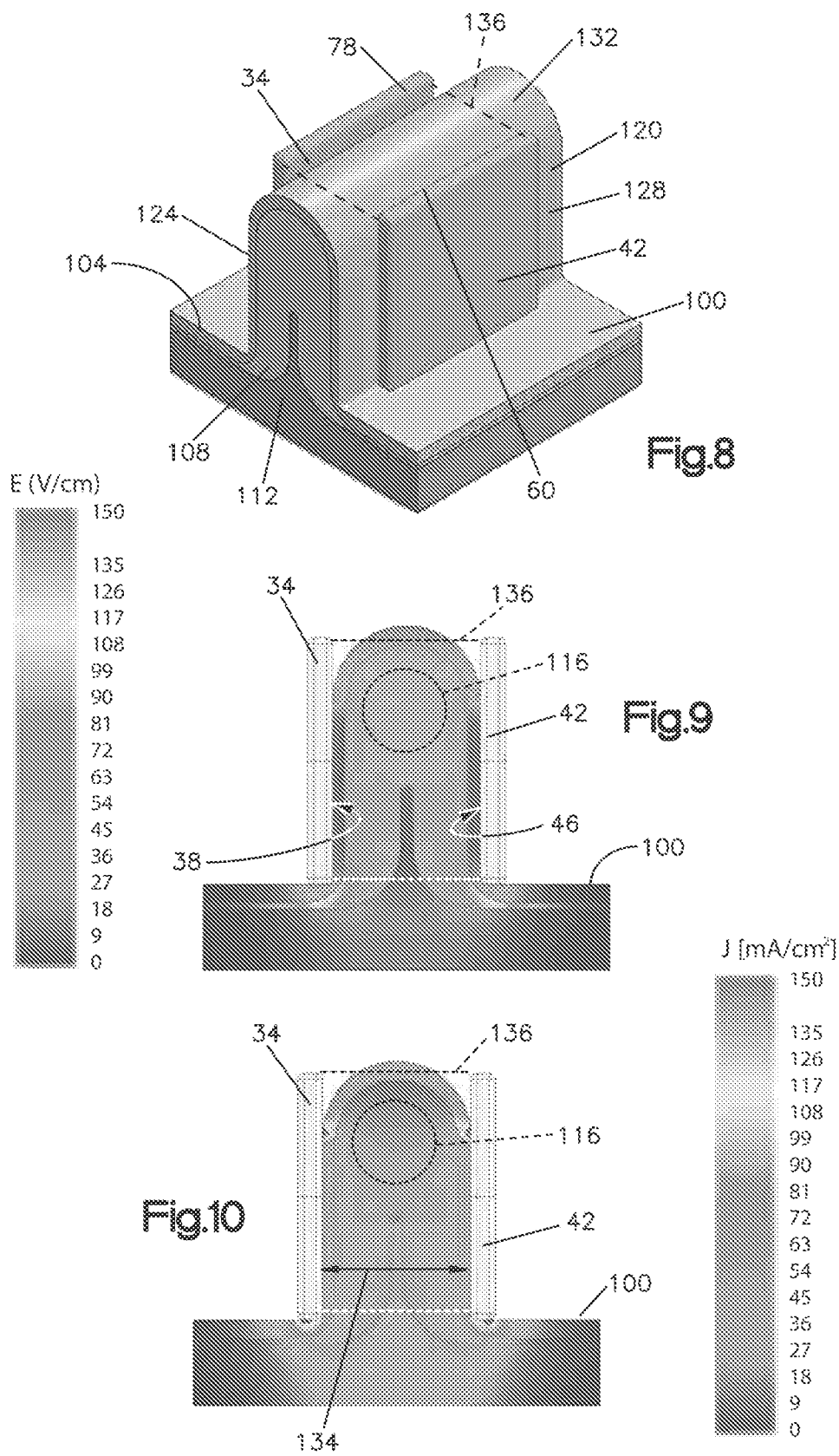

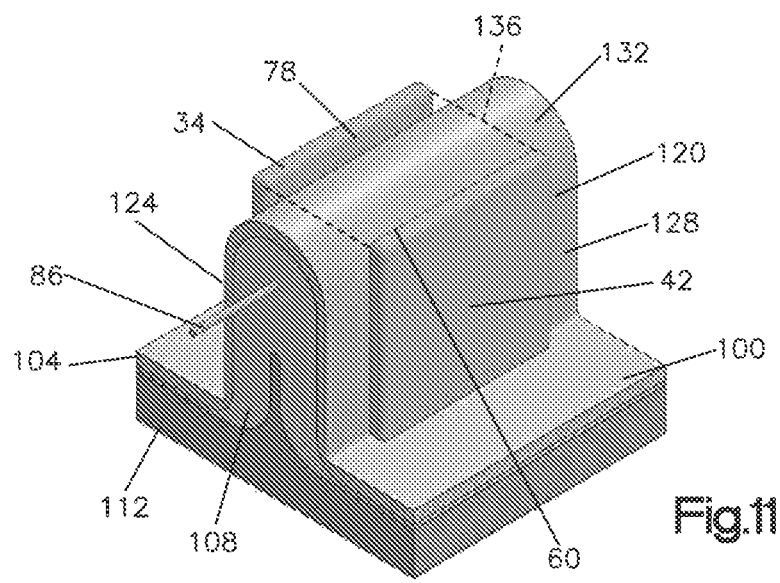
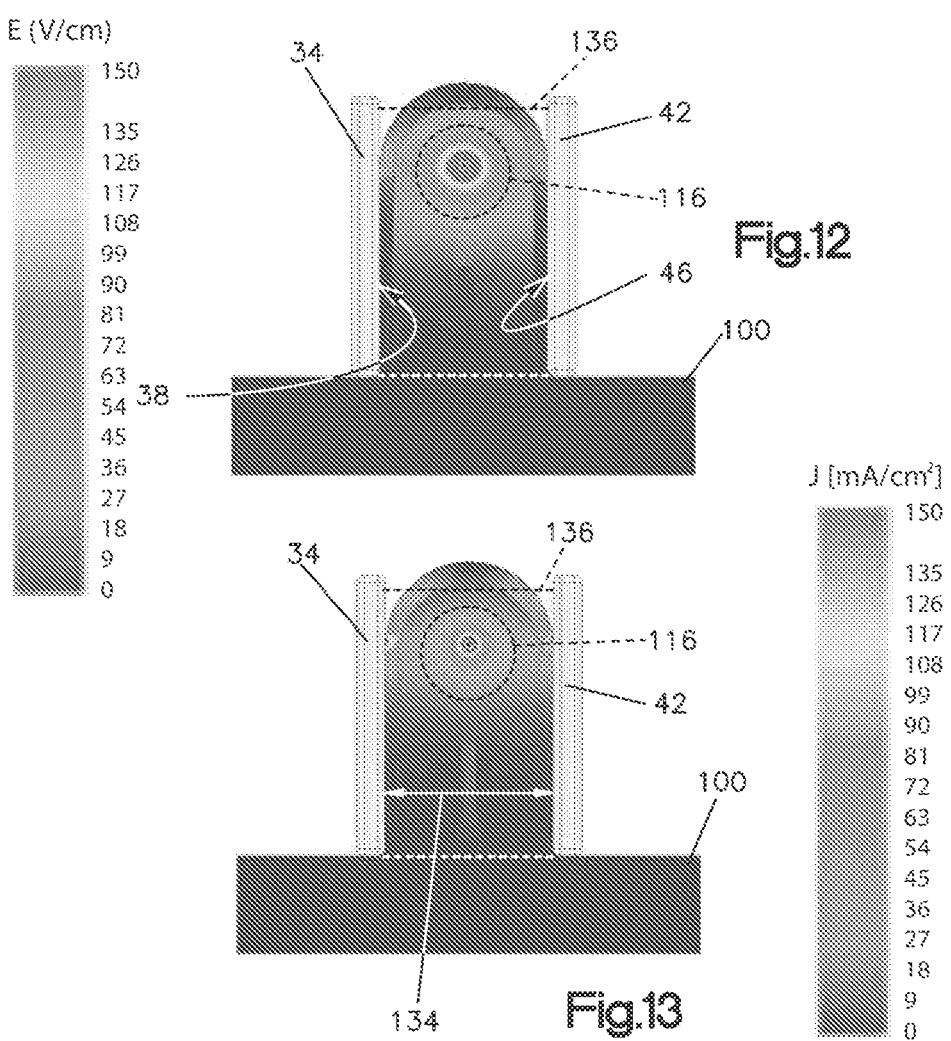

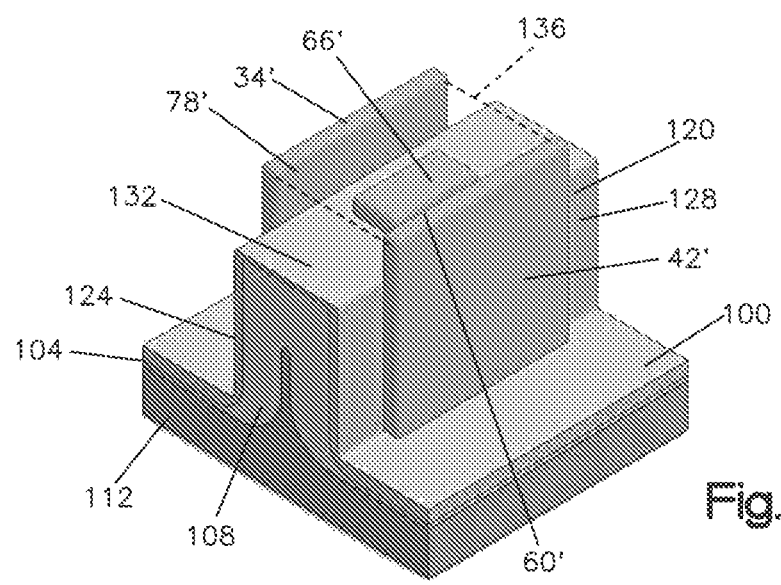
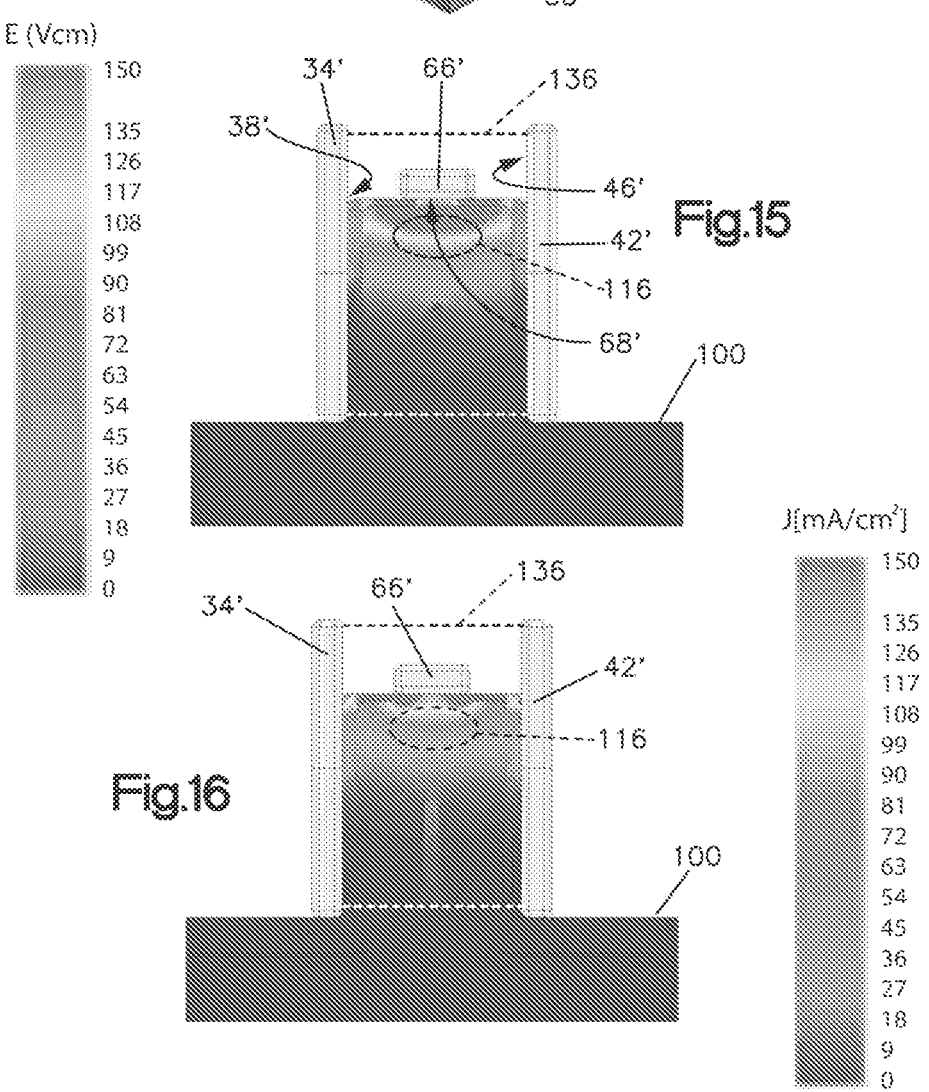

Fig. 28

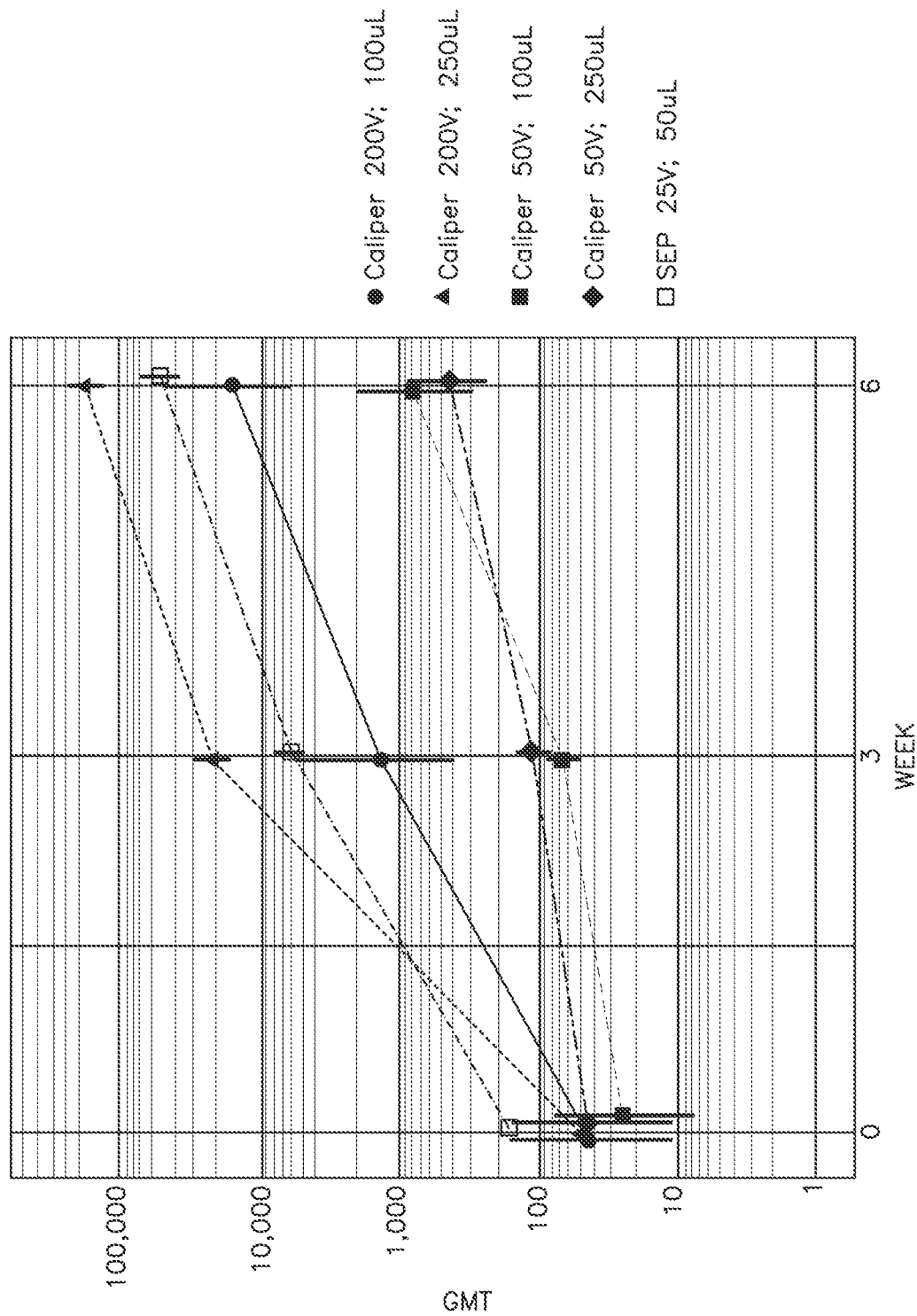

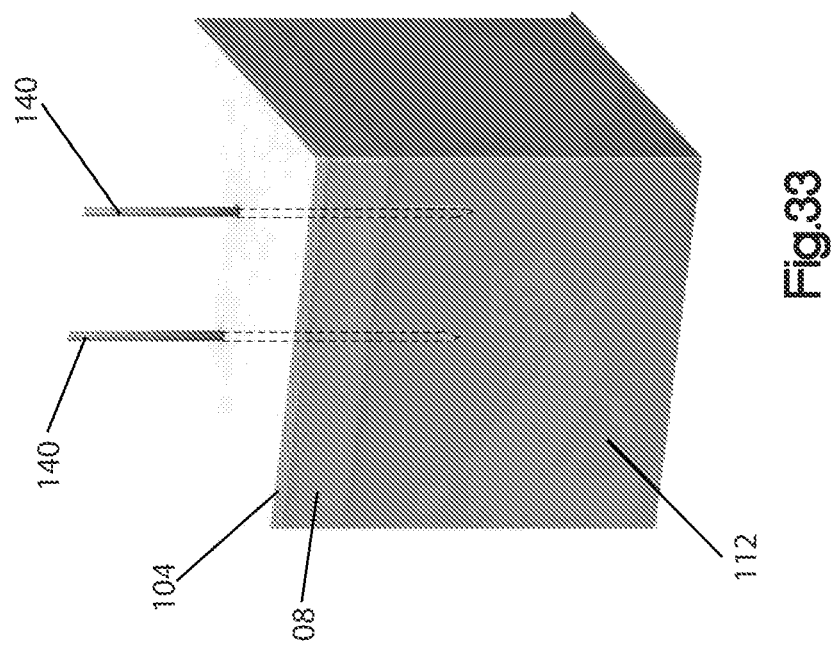
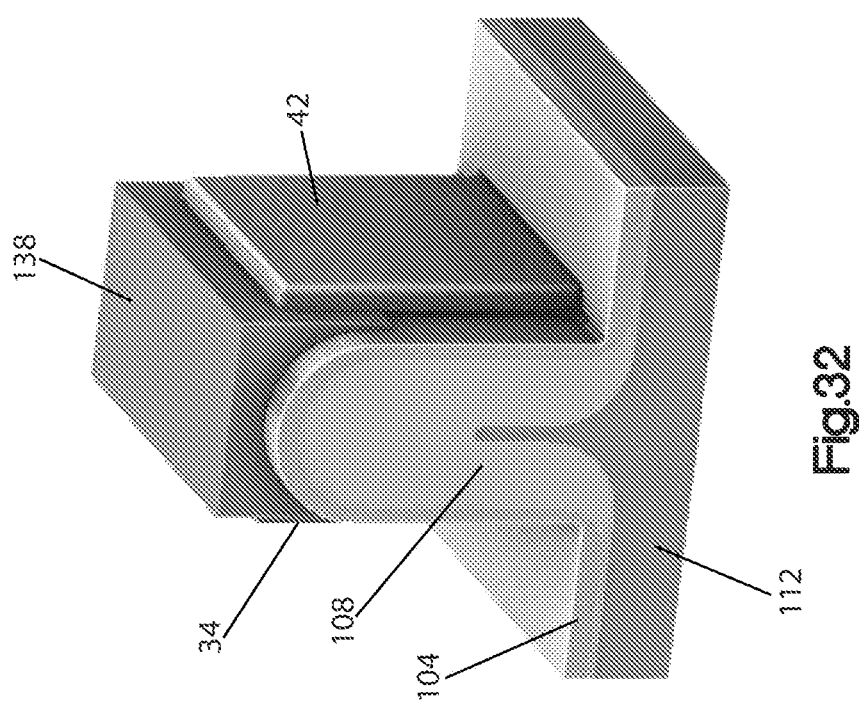

METHOD AND DEVICE FOR MINIMALLY INVASIVE IN VIVO TRANSFECTION OF ADIPOSE TISSUE USING ELECTROPORATION

CROSS REFERENCE TO RELATED APPLICATIONS

This application is the National Stage Application of International Patent Application No. PCT/US2017/052970, filed Sep. 22, 2017, which claims priority to U.S. Provisional Patent Application Ser. Nos. 62/398,932, filed Sep. 23, 2016, entitled "Method and Device for Minimally Invasive In Vivo Transfection of Adipose Tissue Using Electroporation", and 62/480,180, filed Mar. 31, 2017, entitled "Method and Device for Minimally Invasive In Vivo Transfection of Adipose Tissue Using Electroporation", each of which is incorporated in its entirety herein.

TECHNICAL FIELD

This invention relates to a method and device for minimally invasive in vivo transfection of adipose tissue using electroporation.

BACKGROUND

In the 1970's, it was discovered that electrical fields could be used to create pores in cells without causing permanent damage to the cell. This discovery made it possible for large molecules, ions, and water to be introduced into a cell's cytoplasm through the cell wall. In some instances, electroporation can be used in topical treatments, such as head and neck cancer, to introduce chemicals and other compounds into the tumor. During these procedures, the patient may or may not be under general anesthesia so pain and involuntary muscle movement must be minimized.

Skeletal muscle is a well-characterized target for electroporation-mediated (EP) delivery of DNA in vivo. Myocytes are capable of producing and secreting proteins for long periods of time, and it has been repeatedly demonstrated that EP enhanced DNA vaccinations into muscle are able to generate an immune response. Skin is another popular target for EP; it is easily accessed and contains a rich variety of immune cells. The natural immune function of skin and its high rate of cellular turnover typically leads to rapid, strong humoral responses to EP-enhanced DNA delivery. However, applications of muscle EP DNA delivery are complicated by the variable thickness of subcutaneous fat, preventing a "one size fits all" approach since different fat thicknesses result in different needle penetration depths into the muscle tissue.

Historically, adipose tissue has been viewed as an inert tissue primarily used to store energy in the form of lipid droplets. As such, EP-enhanced DNA procedures have not been directed to that specific layer of tissue. However, recent studies have shown that subcutaneous fat actually serves many dynamic roles. Adipose tissue contains many stem cells and immune cells, and acts as an endocrine organ by secreting numerous hormones, secretes many local signals, and contains an elaborate network of capillaries. Any attempts to achieve in vivo transfection of adipose tissue have been limited to surgical techniques that require the administrator to cut away and physically remove samples of the patient's skin to allow contact with the adipose tissue directly. These treatments are extremely invasive and are not suitable for clinical devices.

SUMMARY

A method of electroporating adipocytes in the adipose layer of tissue includes providing a first electrode having a first contact surface which has a first perimeter, providing a second electrode having a second contact surface which has a second perimeter, obtaining a fold of tissue and positioning the fold of tissue between the first electrode and the second electrode such that the first contact surface of the first electrode is facing toward the second contact surface of the second electrode, producing a treatment zone therebetween. The tissue positioned within the treatment zone includes an adipose layer of tissue. The method includes applying an electrical signal to the first electrode and second electrode.

An electroporation device for use with a fold of tissue (which includes a skin layer, an adipose layer, and a smooth muscle layer) includes a frame, a first electrode coupled to the frame, and a second electrode coupled to the frame opposite the first electrode. The first electrode has a first contact surface defining a first perimeter and the second electrode has a second contact surface defining a second perimeter. The first contact surface and the second contact surface define a treatment zone therebetween. The first and second electrodes are configured such that the tissue positioned within the treatment zone includes a skin layer, an adipose layer, and a surface muscle layer.

BRIEF DESCRIPTION OF THE DRAWINGS

FIG. 1 is a schematic view of an electroporation device of the present invention.

FIG. 2 is an alternative embodiment of an electroporation device.

FIG. 3 is a section view taken along line 3-3 of FIG. 2.

FIG. 6 is an electrical field distribution map illustrating the plate electrode of FIG. 5 applied to a fold of tissue.

FIG. 7 is an electrical field distribution map illustrating the plate electrode of FIG. 4 applied to a fold of tissue.

FIG. 8 is a perspective view of a two plate electrode setup applied to a fold of tissue.

FIG. 9 is an E-field simulation of the setup illustrated in FIG. 8.

FIG. 10 is an electric current density map of the setup illustrated in FIG. 8.

FIG. 11 is a perspective view of a needle-in three electrode setup applied to a fold of tissue.

FIG. 12 is an E-field simulation of the setup illustrated in FIG. 11.

FIG. 13 is an electric current density map of the setup illustrated in FIG. 11.

FIG. 14 is a perspective view of a three electrode plate setup applied to a fold of tissue.

FIG. 15 is an E-field simulation of the setup illustrated in FIG. 14.

FIG. 16 is an electric current density map of the setup illustrated in FIG. 14.

FIG. 28. Enzymatic tissue breakdown of adipose tissue (pretreated with enzyme) improves fluid distribution. Dye=methylene blue.

FIG. 31. Immunogenicity Comparison. Electroporation of DNA into adipose and flank skin. Parameters: Voltage and Treatment Volume.

FIG. 32. 3D computer model of a tissue-electrode assembly. Noninvasive EP, with tissue folded between two plate electrodes.

FIG. 33. 3D computer model of another tissue-electrode assembly. Invasive EP using parallel needle electrodes inserted directly into tissue.

FIG. 41: Humoral immunogenicity kinetics of different adipose-EP treatment methods in guinea pigs, with ID-EP (skin) for comparison (n=4). FIG. 42: The same immunogenicity data, grouped by EP voltage (n=8 for adipose HV and adipose L V, n=4 for skin). Data are geometric mean titer±standard error. Adipose-EP treatment parameters are abbreviated as HV=high voltage (200V), LV=low voltage (50V), and for the graph of FIG. 41, the number of DNA injection sites is indicated by a number (1 or 5).

DETAILED DESCRIPTION OF ILLUSTRATIVE EMBODIMENTS

Figure 4:
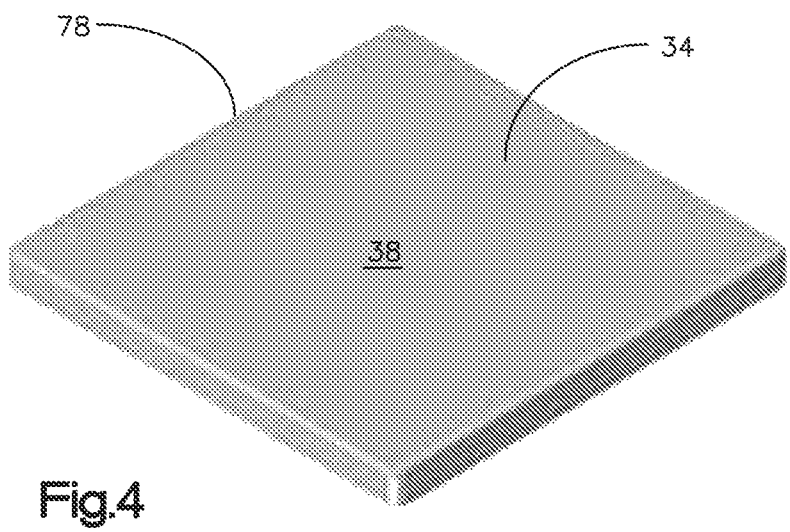
FIG. 4 is a perspective view of a plate electrode.

The inventors have developed an electroporation device and method that target and transfect the adipose layer of tissue in vivo in a minimally invasive way. More specifically, the treatment utilizes a plurality of plate electrodes, in conjunction with an injection mechanism, to expose a region of tissue to a volume of an agent that may be pre-measured, then produce an electrical field within the same region of tissue configured to target the adipose layer causing electroporation in the corresponding adipocytes.

I) DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value)

"Agent" may mean a polypeptide, a polynucleotide, a small molecule, or any combination thereof. The agent may be a recombinant nucleic acid sequence encoding an antibody, a fragment thereof, a variant thereof, or a combination thereof, as detailed in PCT/US2014/070188, which is incorporated herein by reference. "Agent" may mean a composition comprising a polypeptide, a polynucleotide, a small molecule, or any combination thereof. The composition may comprise a recombinant nucleic acid sequence encoding an antibody, a fragment thereof, a variant thereof, or a combination thereof, as detailed in PCT/US2014/070188, which is incorporated herein by reference. The agent may be formulated in water or a buffer, for example. The buffer may be saline-sodium citrate (SSC) or phosphate-buffered saline (PBS), for example. The ionic content of the buffers may increase conductivity, resulting in increased current flow in the targeted tissue. The concentration of the formulated polynucleotide may be between 1 µg and 20 mg/ml. The concentration of the formulated polynucleotide may be 1 µg/ml, 10 m/ml, 25 m/ml, 50 m/ml, 100 m/ml, 250 m/ml, 500 m/ml, 750 m/ml, 1 mg/ml, 10 mg/ml, 15 mg/ml, or 20 mg/ml, for example.

"Antibody" may mean an antibody of classes IgG, IgM, IgA, IgD, or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, a monoclonal antibody, affinity purified antibody, or mixtures thereof which exhibits sufficient binding specificity to a desired epitope or a sequence derived therefrom. The antibody may be a synthetic antibody as described herein.

"Antibody fragment" or "fragment of an antibody" as used interchangeably herein refers to a portion of an intact antibody comprising the antigen-binding site or variable region. The portion does not include the constant heavy chain domains (i.e., CH2, CH3, or CH4, depending on the antibody isotype) of the Fe region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Fragment" as used herein means a nucleic acid sequence or a portion thereof that encodes a polypeptide capable of eliciting an immune response in a mammal. The fragments can be DNA fragments selected from at least one of the various nucleotide sequences that encode protein fragments set forth below. "Fragment" may also refer to a polypeptide sequence or a portion thereof that is capable of eliciting an immune response in a mammal.

A "peptide," "protein," or "polypeptide" as used herein can mean a linked sequence of amino acids and can be natural, synthetic, or a modification or combination of natural and synthetic.

"Polynucleotide" or "oligonucleotide" or "nucleic acid" as used herein means at least two nucleotides covalently linked together. A polynucleotide can be single stranded or double stranded, or can contain portions of both double stranded and single stranded sequence. The polynucleotide can be DNA, both genomic and cDNA, RNA, or a hybrid. The polynucleotide can contain combinations of deoxyribo- and ribo-nucleotides, and combinations of bases including uracil, adenine, thymine, cytosine, guanine, inosine, xanthine hypoxanthine, isocytosine, isoguanine, and synthetic or non-naturally occurring nucleotides and nucleosides. Polynucleotides can be obtained by chemical synthesis methods or by recombinant methods.

"Subject" as used herein can mean a mammal. The mammal can be a human, chimpanzee, guinea pig, pig, macaque, dog, cat, horse, cow, mouse, rat, or other non-human primate.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" can further be defined as a peptide or polypeptide that differs in amino acid sequence by the insertion, deletion, or conservative substitution of amino acids, but retains at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art (Kyte et al., J. Mol. Biol. 1982, 157, 105-132). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly, the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome, or yeast artificial chromosome. A vector can be a DNA or RNA vector. A vector can be a self-replicating extrachromosomal vector, and preferably, is a DNA plasmid.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

II) ELECTROPORATION DEVICE

The invention is directed to an electroporation device including an application device having a plurality of non-invasive plate electrodes. The electroporation device may also include a power supply providing an electroporation signal to the plate electrodes, where, when the electrodes are in electrical contact with a biological sample, the electroporation signal supplied to the electrodes is primarily absorbed by the adipose layer of tissue such that an electrical field is created in the targeted adipose layer. This electrical field causes electroporation to occur within the cell wall of the corresponding adipocytes, thereby increasing the permeability of the cell membranes, and allowing an agent, for example, to be introduced into the cells. As illustrated in FIG. 1, the electroporation device 10 of the present invention includes a housing 14 containing an electroporation (EP) signal generator 18, an applicator 22 removably coupled to the housing 14, and an injection device 26 to inject a pre-determined volume of an agent, such as lipids, into the adipose layer of the sample before electroporation occurs.

As shown in FIG. 1, the hand-held applicator 22 of the present invention includes a frame 30, a first electrode 34 coupled to the frame 30, with the first electrode 34 having a first contact surface 38, and a second electrode 42 coupled to the frame 30, with the second electrode 42 having a second contact surface 46 such that the first contact surface 38 and the second contact surface 46 face one another and are substantially aligned. During use, the applicator 22 is configured to allow the user to manipulate the frame 30 causing the distance between the first contact surface 38 and the second contact surface 46 to change. For the purposes of this application, the distance between the first contact surface 38 and the second contact surface 46 is herein referred to as the "electrode distance 50."

The frame 30 of the applicator 22 includes a base 54, and a plurality of resilient arms 58 each extending from the base 54 to produce a corresponding distal end 62. When assembled, each distal end 62 is configured to have a respective one of the first and second electrodes 34, 42 coupled thereto. In the illustrated embodiment, the arms 58 are configured so that the user may resiliently deform the arms 58, allowing the distal ends 62 and their corresponding electrodes 34, 42, to move. The corresponding electrodes 34, 42, may move independently or in tandem with respect to one another, for example. In the illustrated embodiment, the frame 30 includes two arms 58 (FIG. 1); however in an alternative embodiments, the frame 30 may include more or fewer arms 58 to support the number of electrodes necessary for treatment of the desired target tissue.

As illustrated in FIG. 2, an alternative embodiment of the applicator 22' includes a frame 30' having three arms 58a', 58b', 58c' extending therefrom. More specifically, the frame 30' includes two opposing arms 58a', 58b' configured to support the first and second electrodes 34, 42 such that the first contact surface 38 and the second contact surface 46 face and are substantially aligned with one another. The frame 30' also includes a third arm 58c' configured to support a third electrode 66' such that the third contact surface 68' of the third electrode 66' is positioned perpendicular to the first and second contact surfaces 38', 46'. In the alternative applicator 22', the electrode distance 50' is defined as the distance between the first contact surface 38' and the second contact surface 46' (i.e., the distance between the two contact surfaces facing one another).

The applicator 22 also includes an adjustment mechanism 56 to fix or otherwise manipulate the electrode distance 50 in preparation for and during treatment. The adjustment mechanism 56 includes a rod 70 extending between and threadably engaging both arms 58 of the frame 30 such that rotation of the rod 70 with respect to the arms 58 in a first direction causes the electrode distance 50 to shrink. In contrast, rotation of the rod 70 with respect to the arms 58 in a second direction, opposite the first direction, causes the electrode distance 50 to increase. In the illustrated embodiment, the rod 70 is configured such that the electrode distance 50 will remain fixed unless the rod 70 is rotated by the user (i.e., the threads are not back drivable). In alternative embodiments, the adjustment mechanism 56 may include a latch (not shown) adjustable between a disengaged configuration, where the electrode distance 50 is adjustable by the user, and an engaged configuration, where the electrode distance 50 is fixed. In still other embodiments, the adjustment mechanism 56 may include any form of adjustment mechanism well known in the art and not described herein.

The applicator 22 may also include a sensor 74 in operable communication with the signal generator 18 and configured to determine the electrode distance 50 during operation of the device 10. During use, the sensor 74 sends signals to the signal generator 18 indicating the current electrode distance 50. In some embodiments, the sensor 74 may include a resistance sensor, optical sensor, and the like coupled to the frame 30 of the applicator 22. In the illustrated embodiment, the sensor 74 provides signals to the signal generator 18 allowing the generator 18 to record the electrode distance 50 data and automatically compensate for different electrode distances 50 during treatment. In alternative embodiments the sensor 74 may indicate the distance on a display (not shown) allowing the user to compensate for the electrode distance 50 manually. In still other embodiments, the applicator 22 may be configured such that the user may enter a pre-determined electrode distance 50 into the signal generator 18 whereby the applicator 22 will automatically adjust electrodes 34, 42 to produce the proper electrode distance 50. In still other embodiments, the sensor may be mechanical in nature, displaying the electrode distance 50 on a dial and the like.

Illustrated in FIG. 4, the first plate electrode 34 of the applicator 22 has a first contact surface 38 configured to directly contact the target tissue. The first plate electrode 34 may have any shape. The shape may be rectangular, for example. The first plate electrode 34 also includes a first perimeter 78 extending around and defining the extent of the contact surface 38. During use, the first plate electrode 34 is in operable communication with the signal generator 18 and is configured to engage and form electrical conductivity with the sample tissue during treatment. As such, the plate electrode 34 is able to apply the electroporation signals produced by the signal generator 18 to the target tissue. The plate electrode 34 is also able to detect parameters in the target tissue, such as impedance, voltage, current, and the like, and relay that information back to the signal generator 18 for diagnostics and feedback. In the illustrated embodiment, the first contact surface 38 of the first plate electrode 34 is substantially planar; however, in alternative embodiments, the first contact surface 38 may be curvilinear in contour. In still other embodiments, the first contact surface 38 may include any shape or size intended to maximize the amount of surface area in contact between the electrode 34 and the target tissue. In still other embodiments, the applicator may include a plurality of electrodes 34, each of which includes a first contact surface 38 specifically sized and shaped to correspond with a particular area of a patient or test subject's body. In still other embodiments, the size and shape of the electrodes may be used to focus the distribution of the electric field within the target tissue. In still other embodiments, the first contact surface 38 may include a pattern or knurl formed therein. In still other embodiments, the first contact surface 38 may include a coating or adhesive applied thereto to improve the conductivity or grip between the electrode 34 and the target tissue.

Figure 5:
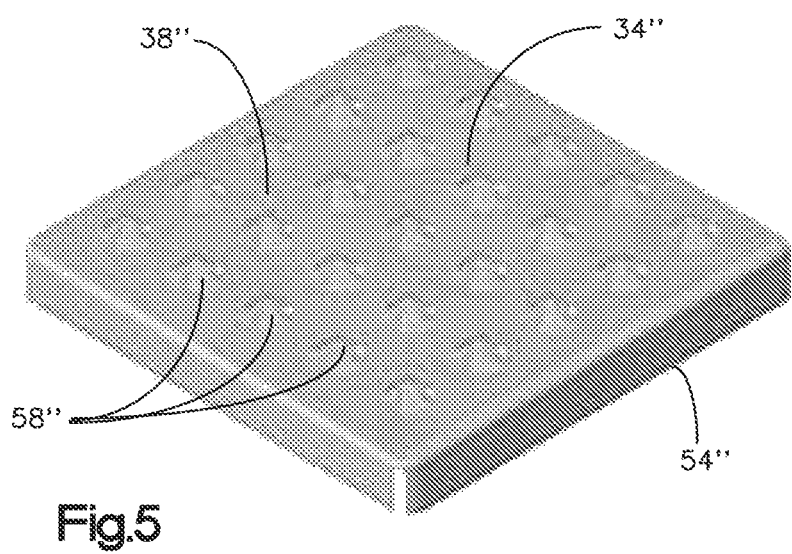
FIG. 5 is a perspective view of an alternative embodiment of a plate electrode.
Figure 17:
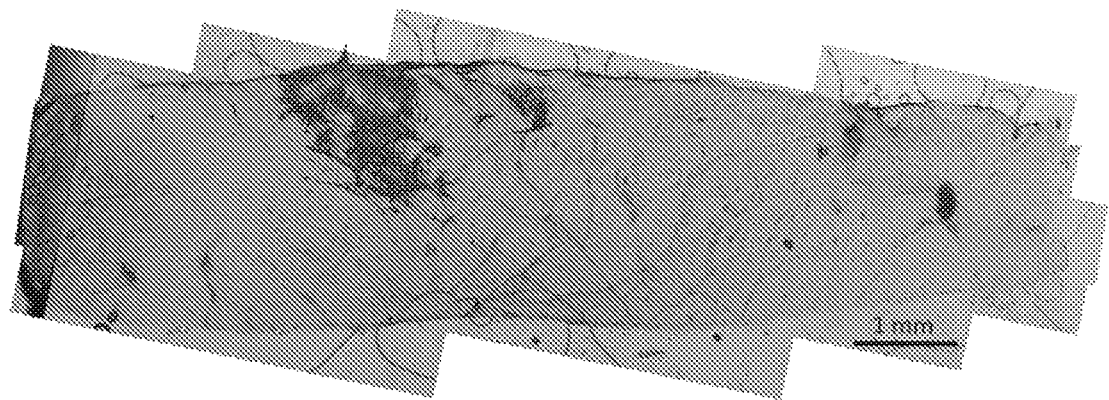
FIG. 17. Guinea pig fat pad data. Plasmid: GFP at 0.5 mg/mL, 250 µ. Electrical parameters: 200V, 3 pulses, 100 msec duration, 200 msec delay. Green areas indicate cells expressing GFP. The tissue section is 100 microns thick.
Figure 18:
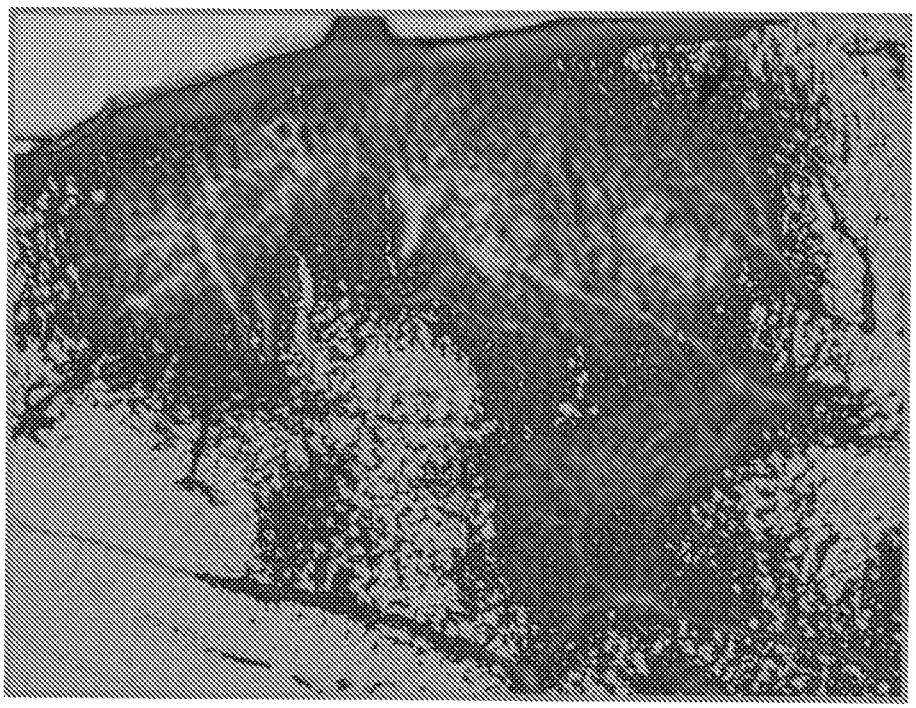
FIG. 18. Higher magnification of FIG. 17.
Figure 19:
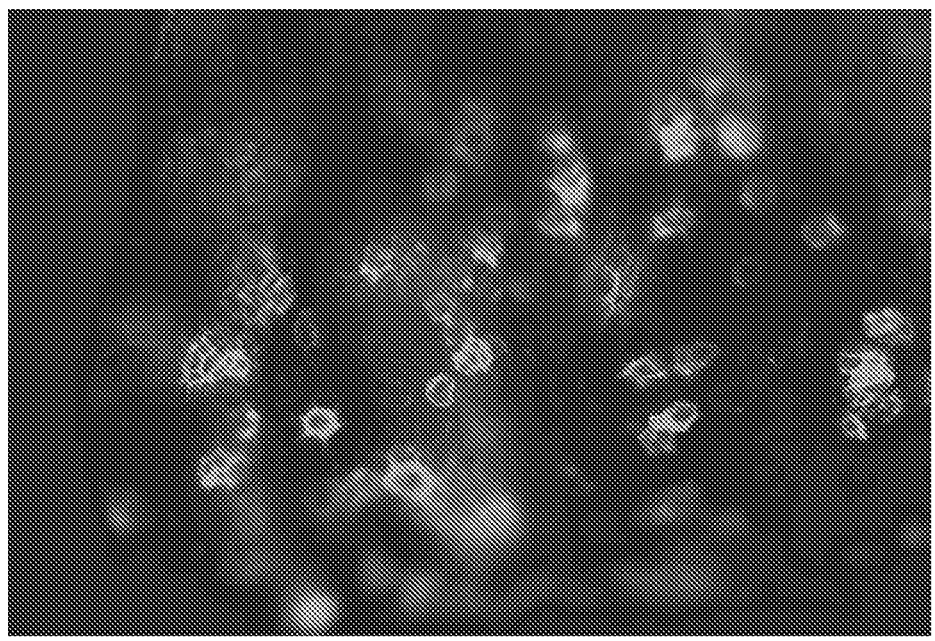
FIG. 19. Guinea pig adipose tissue data. Individual adipocytes expressing GFP around the border of the cells, surrounding the non-expressing interior where the lipid droplet resides. Numerous individual cells are transfected. Plasmid: GFP at 0.5 mg/mL, 250 µl. Electrical parameters: 200V, 3 pulses, 100 msec duration, 200 msec delay.
Figure 20:
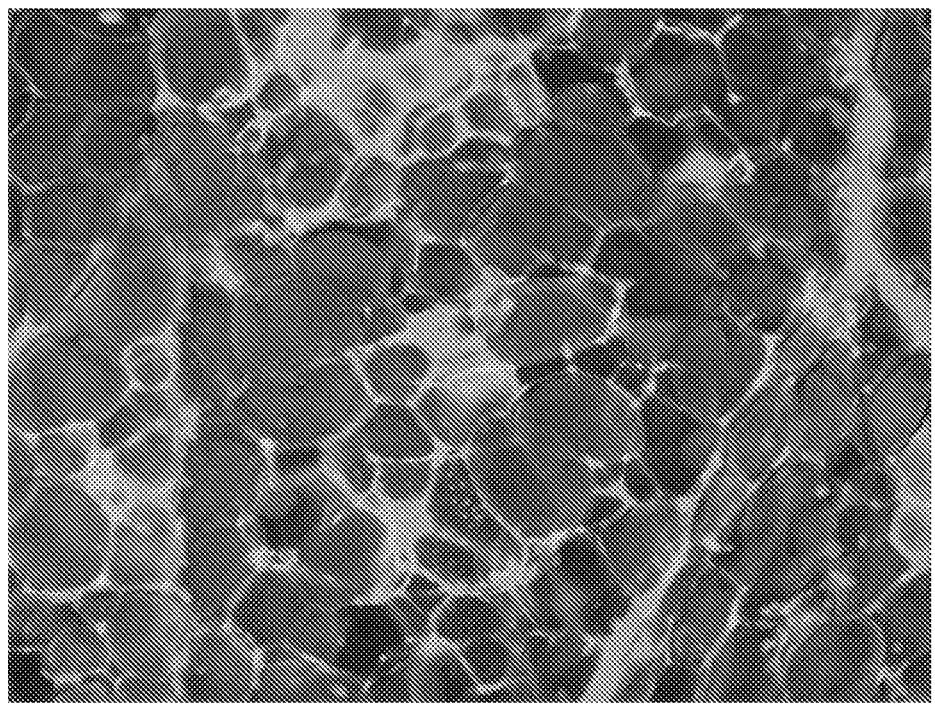
FIG. 20. Rabbit adipose tissue data. Green=GFP expression. Red=lipid (Oil Red O stain). Blue=cell nuclei (DAPI stain). Plasmid: GFP at 0.5 mg/mL, 250 µl. Electrical parameters: 200V, 3 pulses, 100 msec duration, 200 msec delay.
Figure 21:
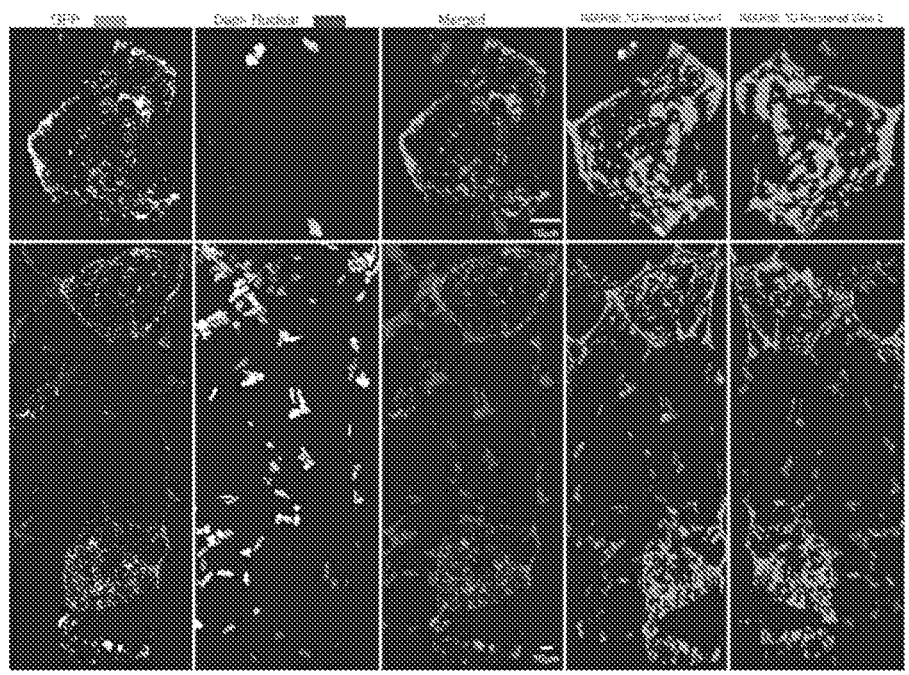
FIG. 21. Confocal images of guinea pig adipose tissue. Numerous cell nuclei are not associated with any transfected areas. The GFP is expressed all around the edge of the cell. Plasmid: GFP at 0.5 mg/mL, 250 µl. Electrical parameters: 200V, 3 pulses, 100 msec duration, 200 msec delay.
Figure 22:
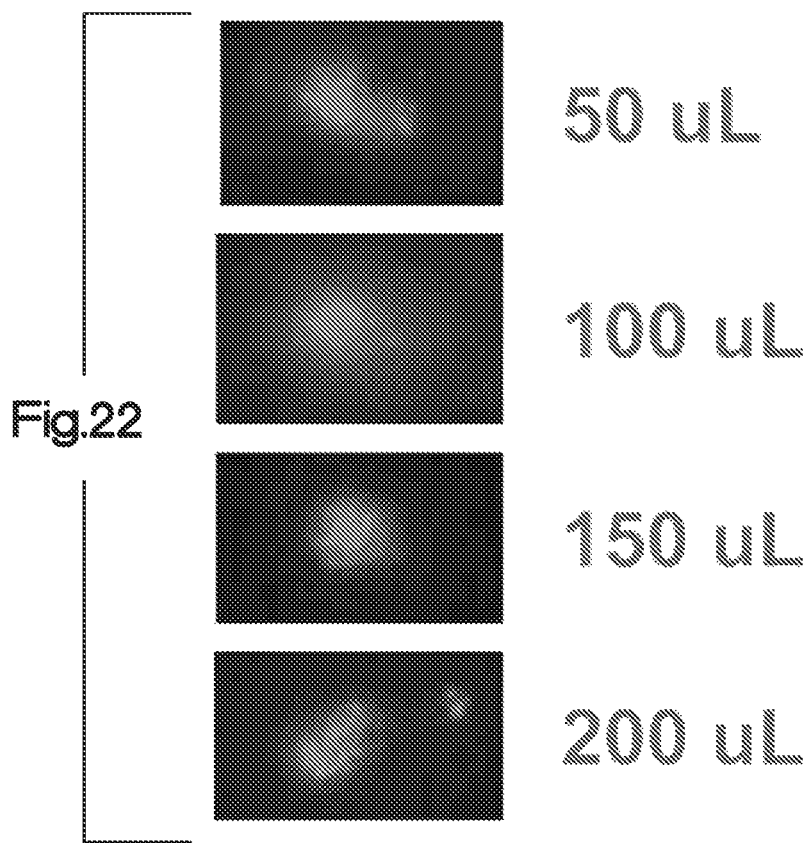
FIG. 22. Transfected area does not change appreciable with injection volume between about 50 µl and 200 µl. Plasmid: Red Fluorescent Protein (RFP) at 0.5 mg/mL, 250 µl. Electrical parameters: 200V, 3 pulses, 100 msec duration, 200 msec delay.
Figure 23:
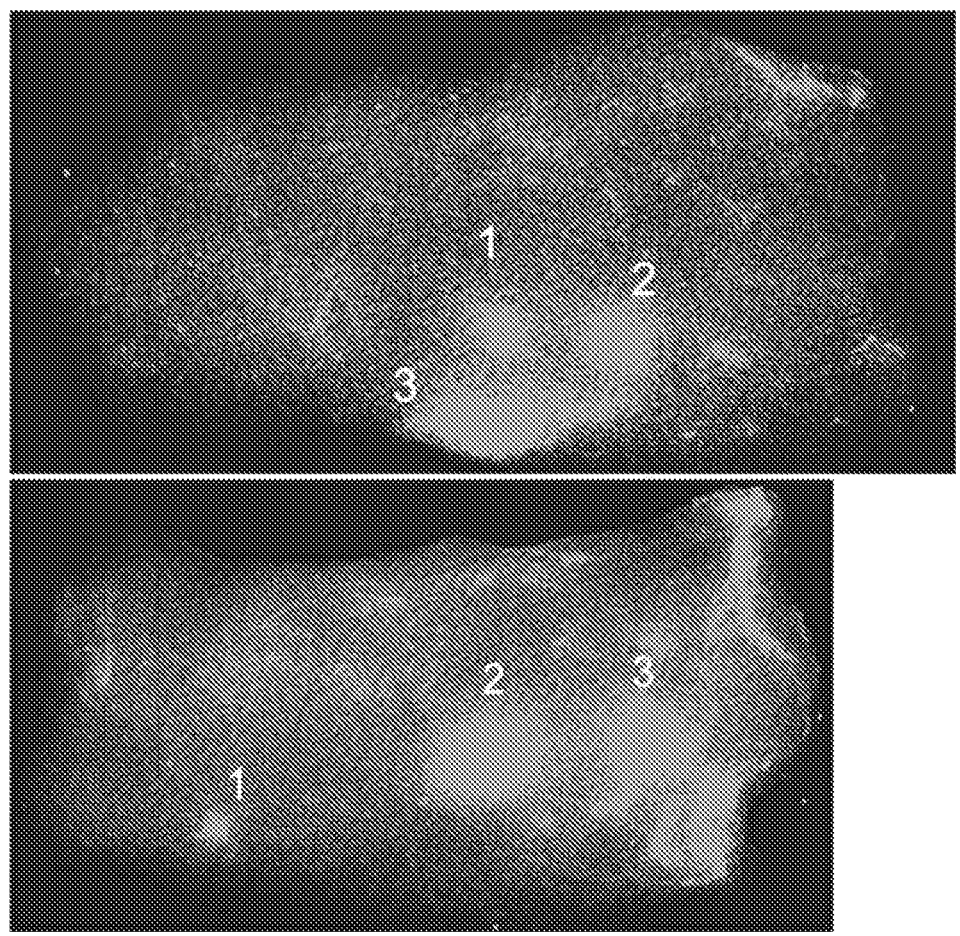
FIG. 23. Multiple injections followed by a single electroporation event. Each injection site is distinctly visible. Numbers indication injection order. Plasmid: GFP at 0.5 mg/mL, 250 µl. Electrical parameters: 200V, 3 pulses, 100 msec duration, 200 msec delay.
Figure 24:
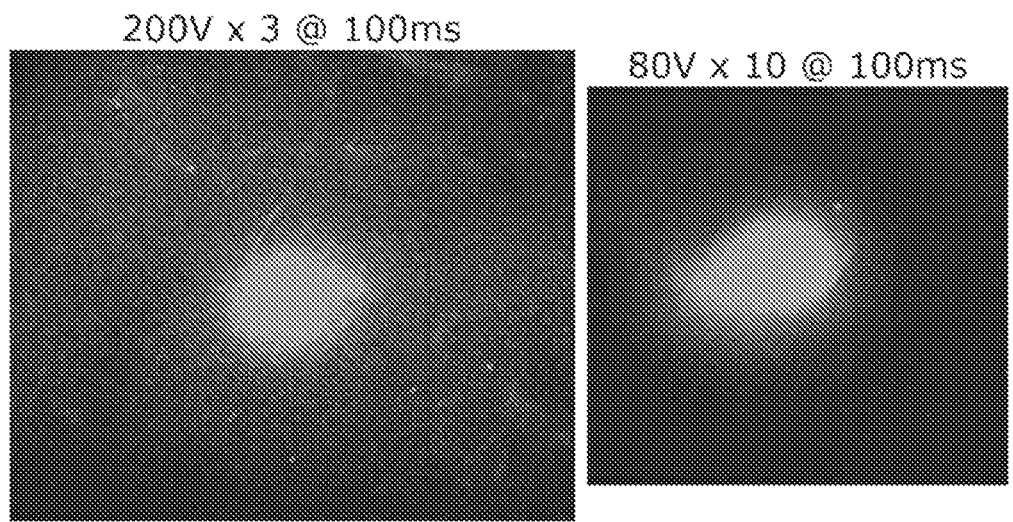
FIG. 24. Varying pulse intensity and number can produce brighter GFP signal (more transfected cells). Plasmid: GFP at 0.5 mg/mL, 250 µl. Electrical parameters: 200V, 3 pulses, 100 msec duration, 200 msec delay.
Figure 25:
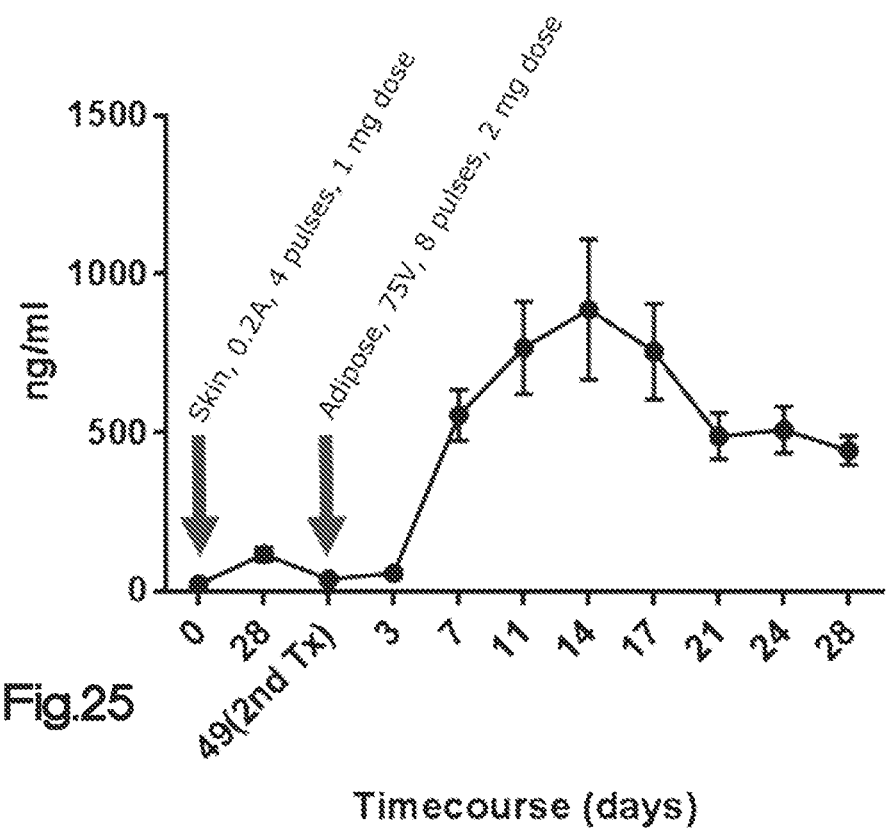
FIG. 25. dMAb delivery into adipose using EP. Hyaluronidase pre-treated 2 hours before DNA EP. Plasmid=pGX9249. Arrows indicate first and second treatments, respectively. X-axis is days since last treatment. Treatment 1: 1 mg total DNA, 200V, 3 pulses, 100 msec duration. Treatment 2: 2 mg total DNA, 75V, 8 pulses, 100 msec duration.

FIGS. 5 and 6 illustrate an alternative embodiment of a plate electrode 34". The plate electrode 34" is substantially similar to and operates in the same manner as the plate electrode 34, described above. As such, only the differences between the two electrodes 34", 34 will be described in detail herein. Best illustrated in FIG. 5, the contact surface 38" of the plate electrode 34" includes a base 54", and a plurality of protrusions 58" each extending substantially normal to the base 54" a protrusion depth 64" to form a distal end 62". During use, the protrusions 58" of the plate electrode 34" press into the target tissue without piercing therethrough allowing the protrusions 58" to disrupt and alter the top layer of skin, improving the electric field distribution within the target tissue (compare FIG. 6 to FIG. 7) and also improving grip. More specifically, the protrusions 58" increase the magnitude of the electric field formed within the target tissue for a given input voltage. While the protrusions 58" of the illustrated embodiment all produce a similar protrusion depth 64' it is understood that each protrusion 58" may be sized differently as necessary to produce the desired conductivity and grip with the target tissue. Still further, the illustrated embodiment includes a protrusion depth 64" of approximately 500 microns, 600 microns, 700 microns, 800 microns, 900 microns, 1 mm, 1.5 mm, 2 mm, 2.5 mm, and 3 mm.

In the illustrated embodiment, each protrusion 58" of the electrode 34" is substantially pyramidal in shape. Each pyramidal protrusion may also has a base width of approximately 500 microns by 500 microns, 600 microns by 600 microns, 700 microns by 700 microns, 800 microns by 800 microns, 900 microns by 900 microns, 1 mm by 1 mm, 1.5 mm by 1.5 mm, 2 mm by 2 mm, 2.5 mm by 2.5 mm, 3 mm by 3 mm. In alternative embodiments, each pyramidal protrusion may also be non-square in base dimensions. In alternative embodiments, each protrusion 58" may form any other shapes configured to press into and deform the target tissue without piercing the tissue during operation. For example, the protrusions 58" may be cylindrical, rectangular, conical, frusto-conical, or frusto-pyramidal in shape. Furthermore, each protrusion 58" may include a width of approximately 500 microns, 600 microns, 700 microns, 800 microns, 900 microns, 1 mm, 1.5 mm, 2 mm, 2.5 mm, or 3 mm, for example.

In still further embodiments, each protrusion 58" may be configured to pierce the target tissue. For example, such protrusions 58" may include a needle (not shown) extending from the base 54". In still other embodiments, such protrusions 58" may be shaped like a hypodermic needle, trochar needle, and the like. In still other embodiments, such protrusions 58" may have a blunt tip or a flat tip. In still other embodiments, each protrusion 58" may be shaped differently than other protrusions 58" on the same electrode.

Illustrated in FIG. 5, the protrusions 58" of the electrode 34" are evenly positioned on the base 58" of the plate electrode 34" in the form of a rectangular array. In alternative embodiments, the protrusions 58" may be positioned in any pattern necessary to provide the necessary conductivity and grip with the target tissue. For example, the protrusions 58" may be positioned in concentric rings (not shown) or other patterns.

Figure 44:
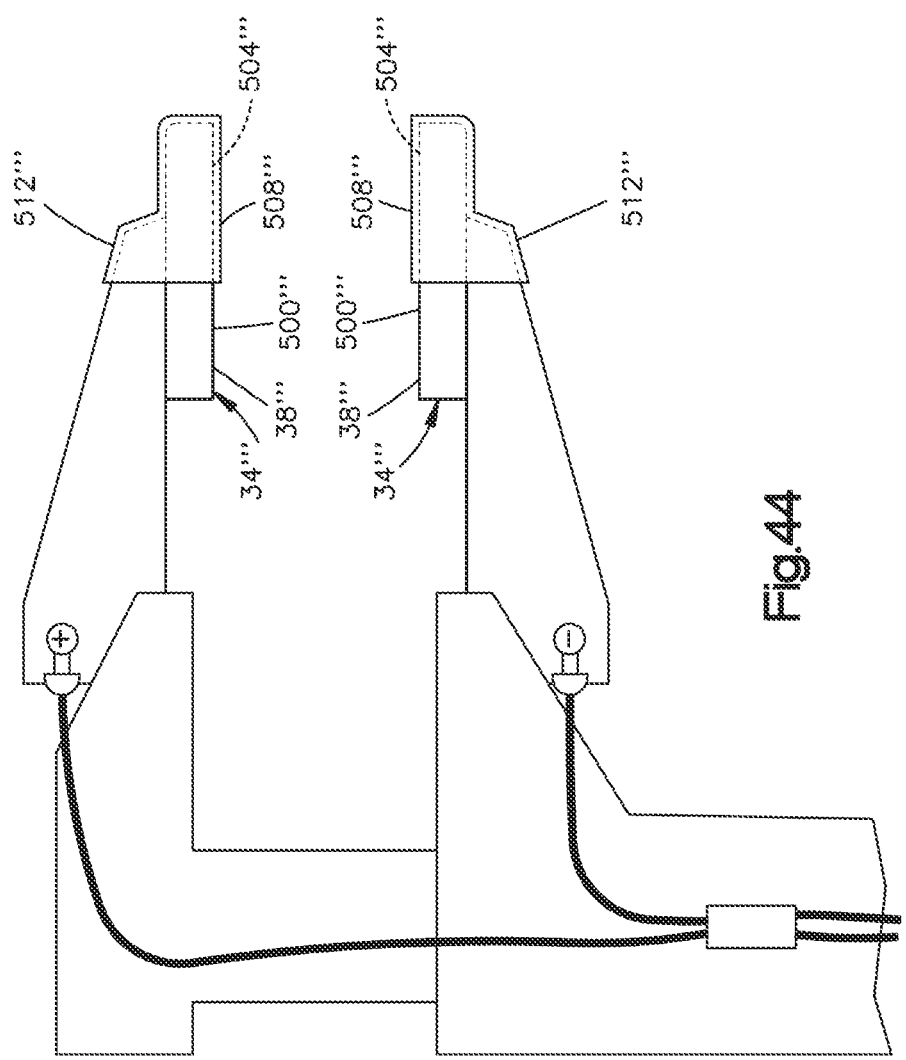
FIG. 44 is a perspective view of an alternative embodiment of plate electrodes coupled to an electroporation device.
Figure 45:
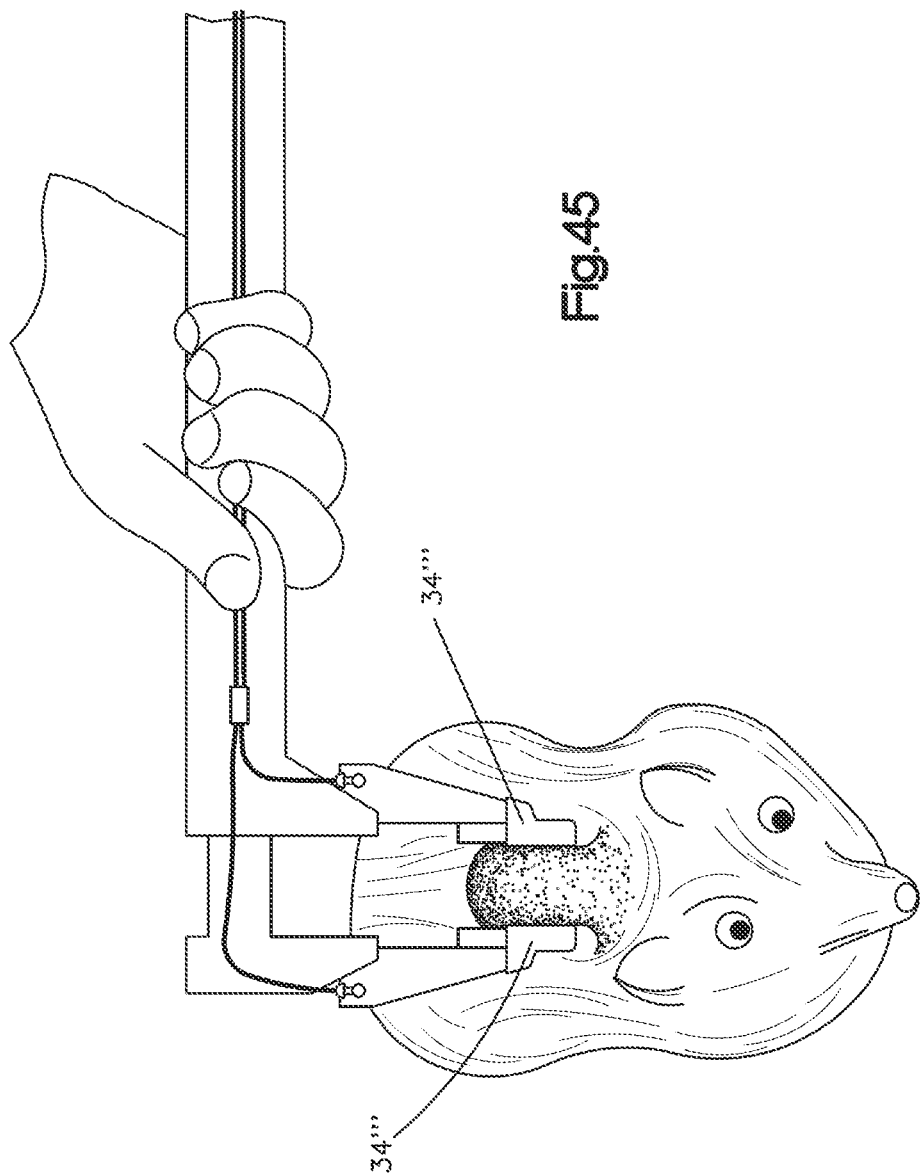
FIG. 45 is a photograph of the electroporation device of FIG. 44 being used on a test subject.
Figure 46:
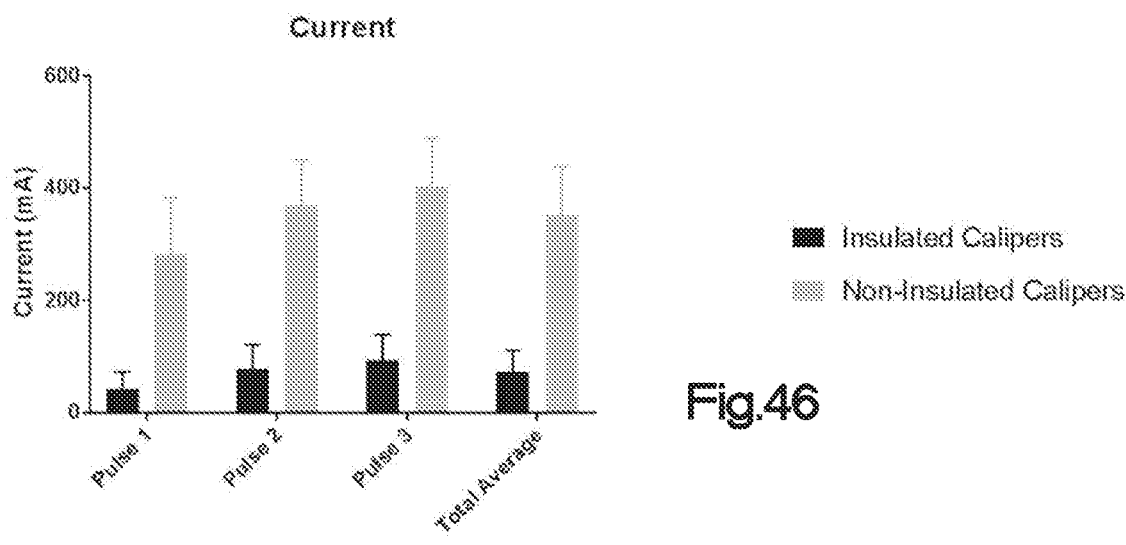
FIGS. 46-48. Electrical data, in particular, current data (FIG. 46), voltage data (FIG. 47), and resistance data (FIG. 48), each averaged from application of both insulated and non-insulated calipers to four guinea pigs.
Figure 47:
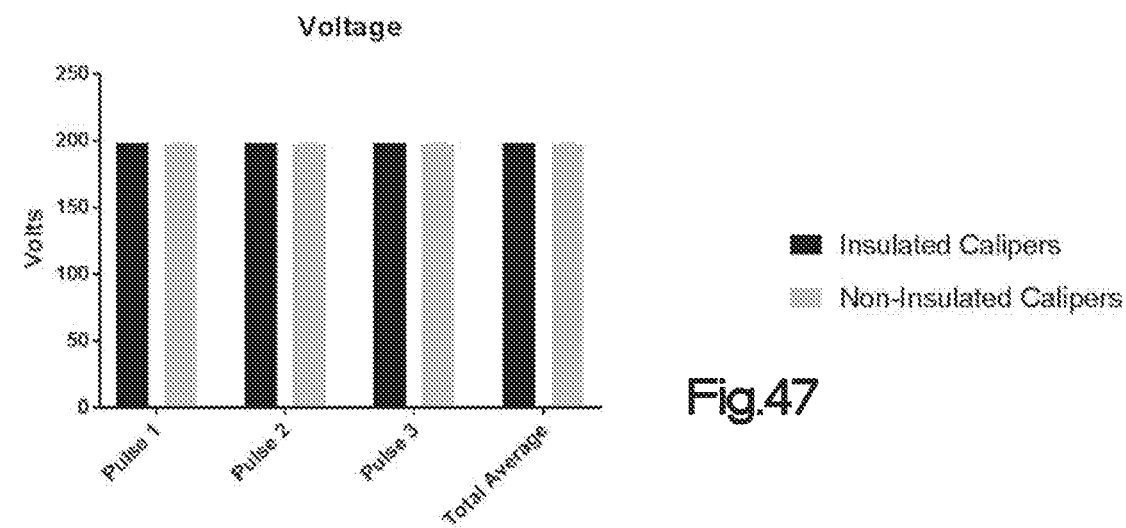
Figure 48:
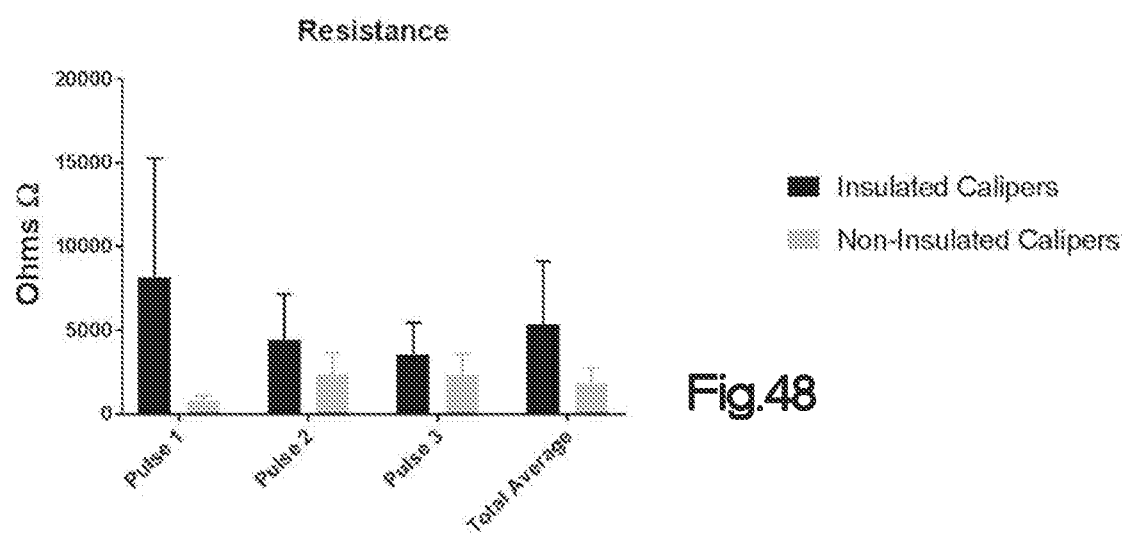

FIGS. 44 and 45 illustrate another alternative embodiment of a plate electrode 34'''. The plate electrode 34''' is substantially similar to and operates in the same manner as the plate electrode 34, described above. As such, only the differences between the two electrodes 34''', 34 will be described in detail herein. Best illustrated in FIG. 44, the contact surface 38''' of the plate electrode 34''' includes one or more non-insulated portions 500, where the contact surface 38''' creates a first resistance with the target tissue when in contact therewith, and one or more insulated portions 504, where the contact surface 38''' creates a second resistance with the target tissue when in contact therewith that is larger than the first resistance. During use, the interaction of the non-insulated and insulated portions 500''', 504''' of the contact surface 38''' with the target tissue effects the resulting electrical field applied to the target tissue. In particular, by insulating at least a portion of the contact surface 38" of the electrode 34", the electrode 34" better focuses the electric field within the adipose layer of the target tissue, thereby decreasing the amount of muscle twitch and pain experienced by the patient. Stated differently, the alternative plate electrode 34''' reduces the amount of current traveling through the muscle when compared to a similarly shaped and sized plate electrode that does not have an insulated portion (see FIGS. 46 through 48; showing difference between an "insulated calipers" where at least one insulated portion 504''' is present, and a non-insulated calipers where no insulated portion 504''' is present).

Illustrated in FIGS. 44 and 45, the insulated portion 504''' of the plate electrode 34''' includes a layer of insulating material 508''' positioned between the contact surface 38''' and the target tissue to increase the resistance therebetween (see FIG. 45). In the illustrated embodiment, the electrode 34''' includes a sheath 512''' formed from insulating material 508''' that is removably positionable over at least a portion of the electrode 34'''. Dependent upon the size and shape of the sheath 512''', different sizes and shapes of the contact surface 38''' may be covered by the insulating material 508'''. In still other embodiments, the insulating material 508''' may be applied to the contact surface 38''' of the electrode 34''' (e.g., like a coating). In still other embodiments, the insulating material 508''' may be applied to the contact surface 38''' with a removable adhesive (not shown).

The second plate electrode 42 is substantially similar to and operates in the same manner as the first plate electrode 34. The second plate electrode 42 includes a second contact surface 46 having a second perimeter 60 defining the extent of the second contact surface 46. As such, the second plate electrode 42 will not be described in detail herein. While the illustrated embodiment shows the second plate electrode 42 being the same size and shape as the first electrode 34, it is understood that the second electrode 42 may be sized and shaped differently than the first electrode 34. Furthermore, the second contact surface 46 of the second electrode 42 may be sized and shaped differently than the first contact surface 38 of the first electrode 34. In still other embodiments, one plate electrode may include protrusions 58" while another electrode may not. Still further, one plate electrode may include an insulated portion 504''' while the other electrode may not.

As illustrated in FIG. 1, the device 10 can further includes an injection device 26 to inject agent into the target tissue at a desired location. More specifically, the injection device 26 includes a reservoir 82 configured to hold a predetermined volume of agent therein, and an injection needle 86 extending from and in fluid communication with the reservoir 82 to produce a distal end 90. During use, the user inserts the injection needle 86 into the target tissue so that the distal end 90 is positioned at the desired depth (i.e., within the adipose layer 104; see FIG. 11). The user may then inject the fluid contained within the reservoir 82 through the needle 86, out the distal end 90, and into the desired tissue. While the illustrated injection device 26 includes a hypodermic needle (i.e., an insulin needle), in alternative embodiments, it is understood that a jet injector or other forms of injection may be utilized.

Furthermore, in some embodiments, the needle 86 of the injection device 26 may be in operable communication with the signal generator 18 and able to perform as an electrode similar to the first and second plate electrodes 34, 42 (see FIG. 1). In such embodiments, the signal generator 18 may be able to both send the treating signal to the needle 86 as well as receive information, such as impedance, current flow, and the like back to the signal generator 18 for diagnostics and feedback purposes.

The injection device 26 may also include a depth limiter (not shown) to control the position of the distal end 90 within the sample tissue. During use, the depth limiter may be set to a predetermined depth so that the depth limiter will stop the distal end 90 of the needle 86 from penetrating beyond the desired depth into the tissue. In some embodiments, the depth limiter may include a hard stop defining a guide hole. In such embodiments, the length of the guide hole dictates the depth the needle penetrates the target tissue. In still other embodiments, the depth limiter may also include an electric coupler to electrically couple the needle 86 with the pulse generator 18.

III) TREATMENT OF ADIPOSE LAYER

The above described device may be used in various therapeutic methods intended to transfect adipose tissue with an agent using electroporation. Each treatment or "setup" provides flexibility regarding the size, shape, and characteristics of the resulting electrical field created within the sample tissue. Each setup also provides various levels of invasiveness.

a) Two Electrode Setup

To administer the treatment via the two-electrode treatment setup, the user first obtains a patient, taking note of the area or region they wish to treat (hereinafter the "tissue region 100"). For the purposes of this application, the tissue region 100 may include skin tissue having, for example, one or more of a skin layer 104, an adipose layer 108, and a smooth muscle layer 112.

Skin Layer. The skin layer may have two parts: an outer epidermis portion and a dermis portion, to which the epidermis may be connected. Beneath the dermis, a subcutaneous layer may exist and may contain areolar and adipose tissues. Fibers from the dermis may extend down into the subcutaneous layer and connect the subcutaneous layer to the skin layer. The subcutaneous layer may be attached to underlying tissues and organs.

Epidermis. The epidermis may be composed of stratified squamous epithelium and contain keratinocytes, melanocytes, and nonpigmented granular dendrocytes (for example, Langerhans' cells and Granstein cells). The keratinocytes may be organized into several layers. The number of layers may depend on location in the body. For example, where exposure to friction is great, the epidermis may have many layers, for example five layers. Where exposure to friction is not great, the epidermis may have less than five layers, for example. The epidermis may have one or more of the following layers: stratum basale, stratum spinosum, stratum granulosum, stratum lucidum, and/or the stratum corneum.

Dermis. The dermis may be composed of connective tissue that contains collagenous and elastic fibers. The dermis may be thick or think depending on the location in the body. For example, the dermis may be thicker in the palms and soles, yet thin in the eyelids. The dermis may contain blood vessels, nerves, glands, and hair follicles. The dermis may have a papillary region or layer, which may consist of loose connective tissue that contains fine elastic fibers. The papillary region may also have dermal papillae that project into the epidermis. These papillae may contain capillaries, corpuscles of touch (or Meissner's corpuscles), which are nerve endings that are sensitive to touch. Dermal papillae may cause ridges in the overlying epidermis.

The remaining portion of the dermis may be the reticular region or layer. This region may contain densely packed connective tissue and bundles of collagenous and coarse elastic fibers. Varying thicknesses of the reticular region may be responsible, at least in part, for differences in the thickness of the skin.

Adipose Layer. The adipose layer or tissue may be a form of loose connective tissue in which adipocytes store fat. An adipocyte may have its cytoplasm and nuclei pushed to the edge of the cell by the droplet of fat within the cell. Each adipocyte may be surrounded by a collagenous basement membrane for structural support, and may be in contact with a capillary. Clusters of adipocytes may be contained within "lobes," which may be held together by collagenous septa. The adipose tissue may be found wherever loose connective tissue is located. The adipose tissue may be in the subcutaneous layer below the skin.

Smooth Muscle Layer. The smooth muscle layer may be located in the walls of hollow internal structures such as, for example, blood vessels. Smooth muscle may also be attached to hair follicles. The smooth muscle layer is non-striated, involuntary muscle tissue and may be influenced by involuntary nerves and some hormones. The smooth muscle layer is a type of muscle layer that is distinct from cardiac muscle tissue and skeletal muscle tissue. Skeletal muscle is attached primarily to bones and may move parts of the skeleton. Skeletal muscle is also striated, because striations, or alternating light and dark bandlike structures are visible when the tissue is examined under a microscope, and voluntary, whereby it can be made to contract and relax by conscious control. Cardiac muscle tissue is striated and involuntary and forms most of the wall of the heart.

With the area of treatment selected, the user obtains the injection device 26 and inserts the needle 86 into the tissue region 100 such that the distal end 90 is positioned within the adipose layer 108. The user then injects a volume of an agent, optionally a pre-measured volume of an agent, into the adipose layer 108 of the tissue region 108, creating an injection site 116. Once the injection is complete, the user removes the needle 86 from the tissue region 100.

With the needle 86 removed, the user manipulates a portion of the tissue region 100 containing the injection site 116 and creates a fold 120 therein. The tissue is manipulated so that the tissue contained within the fold 120 is limited to a skin layer 104, an adipose layer 108, and a smooth muscle layer 112. No skeletal muscle (not shown) is included in the fold 120. The resulting fold 120 includes a first side 124, a second side 128 opposite the first side 124, and a top 132 extending between the first side 124 and the second side 128 (FIG. 8). The fold 120 also defines a fold thickness 134 defined as the distance between the first side 124 and the second side 128.

After preparing the fold 120, the user manipulates the frame 30 or adjustment mechanism 67 of the applicator 22 until the electrode distance 50 is slightly larger than the fold thickness 134. The user then positions the applicator 22 so that each electrode 34, 42 is positioned on opposing sides of the fold 120 with the contact surfaces 38, 46 facing inward (see FIG. 9). More specifically, the user positions the applicator 22 so that the first contact surface 38 of the first plate electrode 34 is in contact with the first side 124 of the fold 120, and the second contact surface 46 of the second plate electrodes 42 is in contact with the second side 128 of the fold 120, creating a treatment zone 136 therebetween. Once in position, the user may increase or decrease the electrode distance 50 to effectively clamp the fold 120 between the two electrodes 34, 42.

For the purposes of this application, the treatment zone 136 is defined as the volume of space positioned between the first and second electrodes 34, 42 and defined on two sides by the first and second contact surfaces 38, 46, and defined on the remaining sides by an imaginary barrier extending between the first perimeter 78 of the first contact surface 38 and the second perimeter 60 of the second contact surface 46 (see FIGS. 8-10). As such, after the user has positioned the first and second electrodes 34, 42 on opposite sides of the fold 120, the treatment zone 136 of the presently described treatment will contain at least a portion of the fold 120 and at least a portion of the injection site 116 therein. In the illustrated embodiment, the tissue positioned within the treatment zone 136 during treatment is limited to a skin layer 104, an adipose layer 108, and a smooth muscle layer 112. The treatment zone 136 does not include any skeletal muscle therein.

While the illustrated embodiment illustrates the contact surfaces 38, 42 of the electrodes 34, 42 being placed in direct contact with the fold 120, it is understood that conductive gel (not shown) or other substances may be utilized to improve the electrical communication between the electrodes 34, 42 and the fold 120.

Once the electrodes 34, 42 are in position, the sensor 74 of the applicator 22 determines the electrode distance 50 and relays that information to the signal generator 18 allowing it to set the parameters of the electroporation signal 150 accordingly. The signal generator 18 may also produce a test signal (i.e., a low voltage pulse) where the resulting current and voltage may be detected by the electrodes 34, 42 and subsequently used by the signal generator 18 to calculate the impedance of the tissue being treated. Furthermore, the data detected by the electrodes 34, 42 during the test signal may also be used to verify that the pulses were fired successfully. To do so, the signal generator 18 compares whether the current flow is maintained for the duration of the pulses, if the timings do not match (i.e., more than one or two data collection points are missing), then the pulses can be considered incomplete. More specifically, at least one of the pulse voltage 158, pulse length 162, number of pulses and/or pulse delay 166 of the electroporation signal may at least partially be determined by the electrode distance 50 (described below). In the illustrated embodiment, the electrode distance 50 is determined automatically by the sensor 74 of the applicator 22. However, in alternative embodiments, the user may manually measure the electrode distance 50 and input the electrode distance 50 into the device 10.

Figure 26:
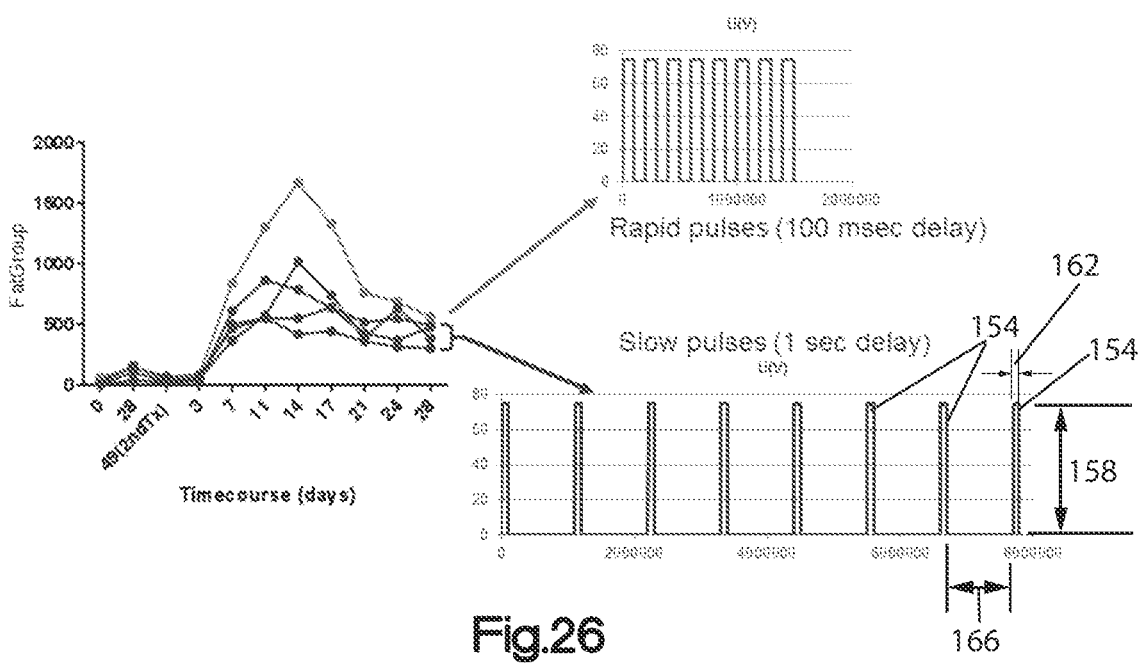
FIG. 26. Same study as FIG. 25, showing individual guinea pig dMAb concentration. The animal highlighted in red received rapid pulses 9100 msec delay) instead of 1 sec delay pulses.
Figure 27:
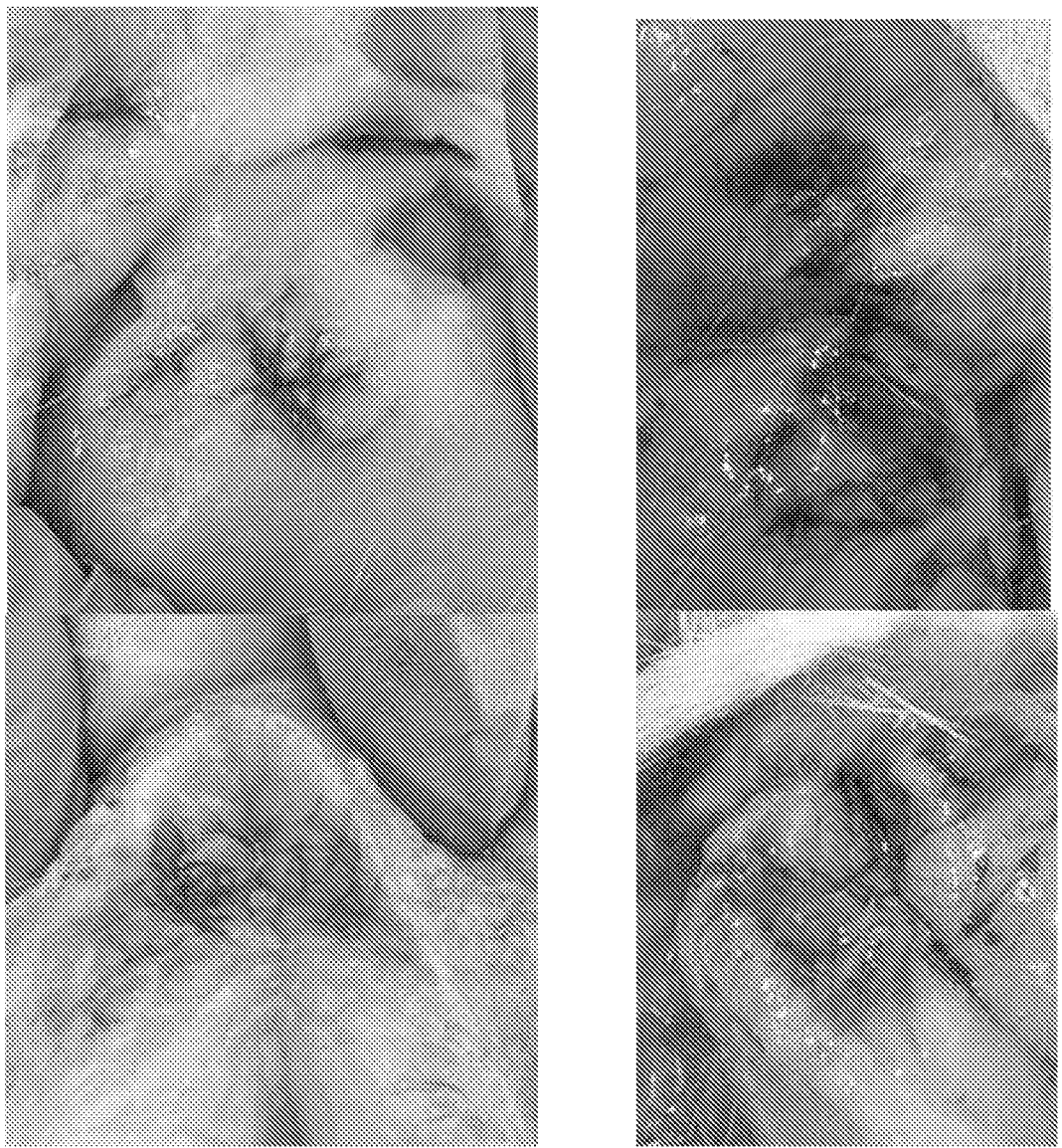
FIG. 27. Insulin needle versus jet injector—fluid distribution in adipose tissue. Dye=methylene blue. No EP.
Figure 29:
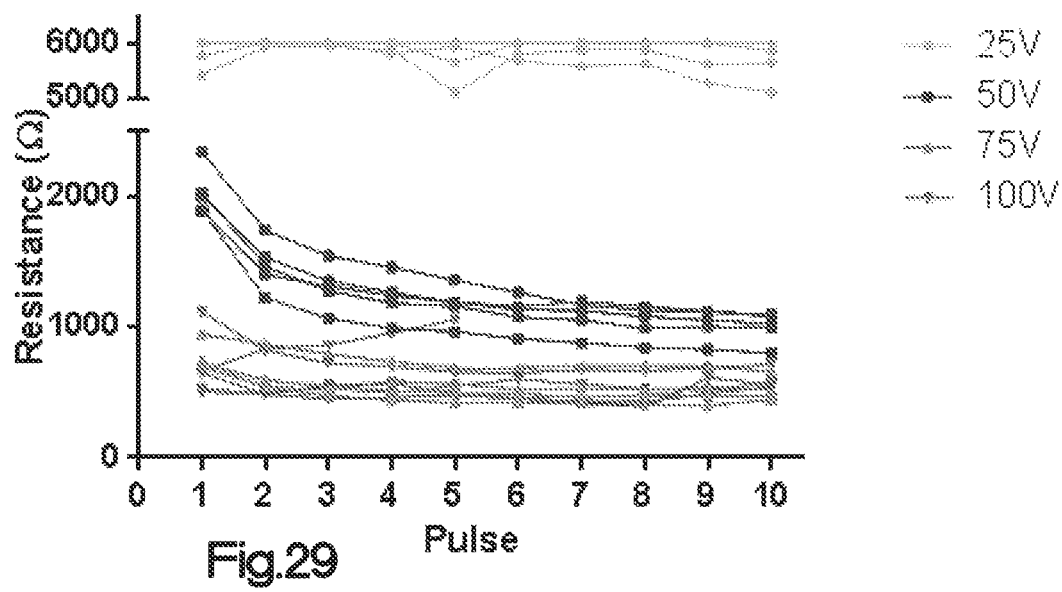
FIGS. 29 and 30. EP Optimization. Note trends in resistance (FIG. 29) and current (FIG. 30) with increasing pulse number. Also note variability in 100 V treatment due to muscle twitch. Pulse duration=100 msec. Pulse delay=100 msec.
Figure 30:
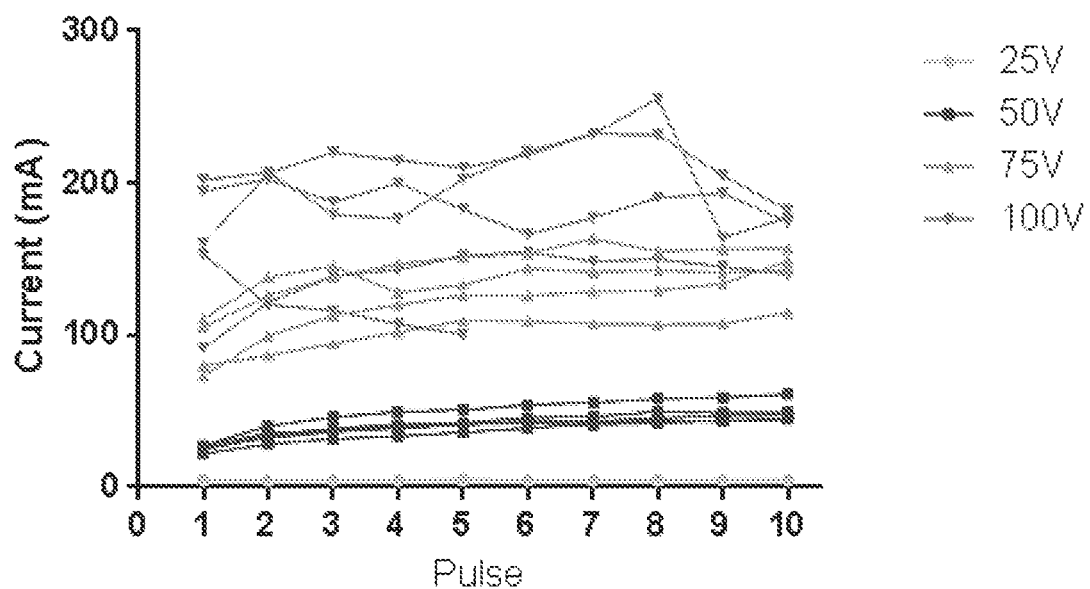

In the illustrated embodiment, the electroporation signal 150 consists of a series of electrical "pulses 154," where each pulse 154 is delivered at a predetermined pulse voltage 158 and lasts a predetermined pulse length 162. Furthermore, each individual pulse 154 is separated in time from adjacent pulses 154 by a pulse delay 166. (FIG. 26). In the illustrated embodiment, the electroporation signal includes a pulse voltage 158 of between approximately 50 V and approximately 200 V. In other embodiment, the signal may include a pulse voltage 158 between approximately 5 V and approximately 10 V. In still other embodiments, the signal may include a pulse voltage 158 of approximately 1 kV. Furthermore, the illustrated electroporation pulse length 162 is approximately 100 microseconds, 200 microseconds, 300 microseconds, 400 microseconds, 500 microseconds, 600 microseconds, 700 microseconds, 800 microseconds, 900 microseconds, 1 millisecond, 10 milliseconds, 50 milliseconds, 75 milliseconds, and 100 milliseconds. Still further, the electroporation pulse delay 166 is approximately 1 millisecond, 50 milliseconds, 100 milliseconds, 500 milliseconds, and 1 second. Still further, each electroporation signal includes between approximately 1 pulse and approximately 10 pulses. Together, in some embodiments the electroporation signal 150 may include 3 pulses at approximately 200 V of approximately 100 milliseconds in duration with 200 milliseconds of delay between pulses. In other embodiments, the electroporation signal 150 may include 3 pulses at approximately 50 V of approximately 100 milliseconds in duration with 200 millisecond delay between pulses. In still other embodiments, the electroporation signal 150 may include 10 pulses at approximately 50 V of 100 milliseconds in duration with 1 second delay between pulses. In still other embodiments, the electroporation signal 150 may include 8 pulses of 75 V of approximately 100 milliseconds of duration with approximately 100 milliseconds of delay between pulses. In still other embodiments, the electroporation signal 150 may include 3 pulses of between approximately 500 V and approximately 1000 V of approximately 10 microseconds and approximately 100 microseconds duration with approximately 100 milliseconds to approximately 1 second delay between pulses. In still other embodiments the electroporation signal may include a single pulse.

After setting the parameters of the electroporation signal, the signal generator 18 of the device 10 sends the desired signal to the first and second electrodes 34, 42 such that one of the first electrode 34 acts as one of the positive electrode or the negative electrode while the second electrode 42 act as the other of the positive electrode or the negative electrode. More specifically, the signal generator 18 may adjust the parameters of the electroporation signal 150 at least partially dependent upon the impedance value detected and the electrode distance 50. Upon receiving the electroporation signal, the electrodes 34, 42 conduct the signal in series to the fold 120 creating an electric field therein (FIGS. 9 and 10). The resulting electric field is concentrated in the adipose layer 108 creating a transfection region within the fold 120. More specifically, the electric field may create a transfection region that is substantially spherical or ellipsoid in shape. However, in alternative embodiments, the size and shape of the transfection region may at least partially depend upon the electric field distribution within the target tissue and the location and quantity of agent that was injected into the target tissue. Furthermore, current freely flows through the underlying muscle layer 112 and is relatively low near the injection site 116 when compared to a similar treatment conducted by penetrating needle electrode configurations commonly used for subcutaneous or intramuscular electroporation delivery. Such characteristics of the electric field are potentially beneficial for treatments where immune response is not desired.

After electroporation is complete, the electrodes 34, 42 may be removed from the fold 120.

b) Needle-In Three Electrode Setup

To administer the treatment via the three electrode setup, the user first obtains a patient, taking note of the tissue region 100 they wish to treat. For the purposes of this application, the tissue region 100 may include skin tissue having, for example, one or more of a skin layer 104, an adipose layer 108, and a smooth muscle layer 112, as described in detail above. With the tissue region 100 selected, the user manipulates a portion of the tissue region 100 and creates a fold 120 therein. More specifically, the user manipulates the tissue region 110, creating a fold 120 of tissue that includes a skin layer 104, an adipose layer 108, and a smooth muscle layer 112. No skeletal muscle is included in the fold 120. Furthermore, the resulting fold 120 of tissue includes a first side 124, a second side 128 opposite the first side 124, and a top 132 extending between the first side 124 and the second side 128. The fold 120 also defines a fold thickness 134 defined as the distance between the first side 124 and the second side 128.

With the fold 120 prepared, the user obtains the injection device 26 and inserts the needle 86 lengthwise through the fold 120 substantially parallel to the first side 124 and the second side 128. The user then injects a pre-measured volume of agent into the adipose layer 108 of the tissue region 100, creating an injection site 116. Once the injection is complete, the user does not remove the needle 86 from the tissue 100.

With the injection site 116 created and with the needle 86 still positioned in the tissue 100, the user manipulates the frame 30 or adjustment mechanism 56 of the applicator 22 until the electrode distance 50 is slightly larger than the fold thickness 134. The user then positions the applicator 22 so that each electrode 34, 42 is positioned on opposing sides of the fold 120 (see FIG. 11-13). More specifically, the user positions the applicator 22 so that the first contact surface 38 of the first plate electrode 34 is in contact with the first side 124 of the fold 120, and the second contact surface 46 of the second plate electrodes 42 is in contact with the second side 128 of the fold 120, creating a treatment zone 136 therebetween (described above; see FIGS. 11-13).

While the illustrated embodiment illustrates the contact surfaces 38, 46 of the electrodes 34, 42 being placed in direct contact with the fold 120, it is understood that conductive gel (not shown) or other substances may be utilized to improve the electrical communication between the electrodes 34, 42 and the fold 120.

Once the electrodes 34, 42 are in position, the sensor 74 of the applicator 22 determines the electrode distance 50 and sets the parameters of the electroporation signal accordingly (described above). The signal generator 18 may also produce a test signal (described above) where the resulting current and voltage may be detected by the electrodes 34, 42 or needle 86 and subsequently used by the signal generator 18 to calculate the impedance of the tissue being treated. In the illustrated embodiment, the electroporation signal 150 consists of a series of electrical pulses 154, where each pulse 154 is given at predetermined a pulse voltage 158 and lasts a predetermined pulse length 162. Furthermore, each individual pulse 154 is separated in time from adjacent pulses 154 by a pulse delay 166. (see FIG. 26). In the illustrated embodiment, the electroporation signal includes a pulse voltage 158 of between approximately 5 V and approximately 500 V. The pulse voltage may be, for example, 5V, 10V, 20V, 40V, 60V, 80V, 100V, 150V, 200V, 250V, 300V, 350V, 400V, 450V, or 500V. Furthermore, the illustrated electroporation pulse length 162 is between approximately 1 microsecond and approximately 100 milliseconds. Still further, the electroporation pulse delay 166 is between approximately 10 millisecond and approximately 1 second. Still further, each electroporation signal includes between approximately 1 and approximately 10 pulses. In alternative embodiments, the parameters of the electroporation signal 150 may be altered to allow optimal performance for different agents. Signal parameters may be adjusted depending on the agent being used, the degree of transfection, and tissue damage desired. For example, dMAb constructs generally require lower voltage, shorter pulse duration, and longer inter-pulse delays, while DNA vaccines generally require higher voltage, shorter delay, and longer pulses.

After setting the parameters of the electroporation signal, the signal generator 18 of the device 10 sends the electroporation signal to the first electrode 34, the second electrode 42, and the needle 86 such that the needle 86 acts as one of the positive electrode or the negative electrode while the first and second electrodes 34, 42 together, act as the other of the positive electrode or the negative electrode. Upon receiving the electroporation signal, the electrodes 34, 42 and needle 86 conduct the signal to the fold 120 creating an electrical field therein (FIGS. 12 and 13). The resulting electric field is concentrated in the adipose layer 108 around the needle 86, decreasing in strength radially therefrom. The electric field also creates a transfection region that tracks along the needle in a very elongated ellipsoid shape. Furthermore, electrical current is highest around the needle 86.

After electroporation is complete, the electrodes 34, 42 and needle 86 may be removed from the fold 120.

c) Three Plate Setup

To administer the treatment with the three plate setup, the user first obtains a patient, taking note of the tissue region 100 they wish to treat. For the purposes of this application, the tissue region 100 may include skin tissue having, for example, one or more of a skin layer 104, an adipose layer 108, and a smooth muscle layer 112 as described in detail above. With the area of treatment selected, the user obtains the injection device 26 and inserts the needle 86 into the tissue region 100 such that the distal end 90 is positioned within the adipose layer 108. The user then injects a pre-measured volume of agent into the adipose layer 108 of the tissue region 108, creating an injection site 116. Once the injection is complete, the user removes the needle 86 from the tissue region 100.

With the needle 86 removed, the user obtains a portion of the tissue region 100 containing the injection site 116 and creates a fold 120 that includes the injection site 116, a skin layer 104, an adipose layer 108, and a smooth muscle layer 112. No skeletal muscle is included in the fold 120. Furthermore, the resulting fold 120 of tissue includes a first side 124, a second side 128 opposite the first side 124, and a top 132 extending between the first side 124 and the second side 128 of the fold 120. The fold 120 also defines a fold thickness 134 defined as the distance between the first side 124 and the second side 128.

After preparing the fold 120, the user manipulates the frame 30' or adjustment mechanism 56' of the applicator 22' until the electrode distance 50' is slightly larger than the fold thickness 134. The user then positions the applicator 22' so that the first contact surface 38' of the first plate electrode 34' is in contact with the first side 124 of the fold 120, and the second contact surface 46' of the second plate electrodes 42' is in contact with the second side 128 of the fold 120, creating a treatment zone 136 therebetween (described above). The user also positions the third plate electrode 66' so that the third contact surface 68' is in contact with the top 132 of the fold 120 and generally positioned between the first and second electrodes 34', 42' (see FIGS. 14-16) such that the third plate electrode 66' does not directly contact either the first or second electrodes 34', 42'.

While the illustrated embodiment illustrates the contact surfaces 3 8', 46', 68' of the electrodes 34', 42', 66' being placed in direct contact with the fold 120, it is understood that coupling or conductive gel (not shown) or other substances may be utilized to improve the electrical communication between the electrodes 34', 42', 66' and the fold 120.

Once the electrodes 34', 42', 66' are in position, the sensor 74' of the applicator 22' determines the electrode distance 50 between the first and second electrodes 34', 42' and sets the parameters of the electroporation signal accordingly (described above). The signal generator 18 may also produce a test signal (described above) where the resulting current and voltage may be detected by the electrodes 34', 42', 66' and subsequently used by the signal generator 18 to calculate the impedance of the tissue being treated. In the illustrated embodiment, the electroporation signal consists of a series of electrical "pulses 154," where each pulse 154 is given at predetermined a pulse voltage 158 and last a predetermined pulse length 162. Furthermore, each individual pulse 154 is separated by in time by adjacent pulses 154 by a pulse delay 166 (see FIG. 26). In the illustrated embodiment, the electroporation signal includes a pulse voltage 158 of between approximately 5 V and approximately 500 V. Furthermore, the illustrated electroporation pulse length 162 is between approximately 1 microsecond and approximately 100 milliseconds. Still further, the electroporation pulse delay 166 is between approximately 10 millisecond and approximately 1 second. Still further, each electroporation signal includes between approximately 1 and approximately 10 pulses.

After setting the parameters of the electroporation signal, the device 10 applies the electroporation signal to the first, second, and third electrodes 34', 42', 66' such that the first and second electrodes 34', 42' act as one of the positive electrode and the negative electrode while the third electrode 66' acts as the other of the positive electrode and the negative electrode. Upon receiving the electroporation signal, the electrodes 34', 42', 66' conduct the signal in series to the fold 120 creating an electrical field therein (FIGS. 15 and 16). The resulting electric field is strongest just below the third plate electrode 66' and decreases in strength with increasing tissue depth. Furthermore, electric current is strong in the skin layer 104 and much weaker in the adipose layer 108 creating a desirable balance between a strong electric field while maintaining a lower current at the injection site. Such electrical fields are generally optimal for DNA injections in shallow subcutaneous fat.

After electroporation is complete, the electrodes 34', 42', 66' may be removed from the fold 120.

IV) EXAMPLES

Example 1. Experimental Results. In vivo treatments were performed on subcutaneous fat pads of female Hartley Guinea Pigs using a variation of the above described treatment. During the experiment, the user shaved the hair near the treatment area proximate the back of the guinea pig's neck. Afterwards, hair removal cream was used to completely remove any remaining stubble from the treatment area. Plasmids were then injected into the adipose layer of the treatment area using an insulin syringe, creating an injection site. The injection site and skin tissue of the treatment area were then manipulated, separating the skin, adipose, and smooth muscle layers from any skeletal muscle. The resulting fold of skin was then positioned between a pair of plate electrodes, each electrode having the corresponding contact surface covered in conductive gel. Finally, electrical pulses were sent to the plate electrodes, where one plate electrode acted as the positive electrode and the other plate electrode acted as the negative electrode. After the treatment was complete, samples of the tissue in the treatment area were taken for analysis (see FIGS. 17-30).

Dye injection studies demonstrated that injectate preferentially travels down collegenous septa surrounding adipose lobes, and these observations were consistent with GFP transfection patterns. To demonstrate section of coded proteins, adipose-targeted EP treatment was performed using DNA encoding monoclonal antibodies (dMAbs), which led to detectable systemic levels of protein. Finally, adipose-targeted EP DNA vaccination of plasmid encoding H1N1 nucleoprotein was shown to be immunogenic. Compared to traditional intramuscular routes, adipose-targeted EP DNA vaccinations may offer tolerability advantages due to the lower voltages, shallower injections, and noninvasive electrodes being used.

At higher magnification, a "honeycomb" pattern characteristic of adipocytes could be seen in bright green due to the numerous transfected adipocytes. Also noted were bright green collagenous septa as solid green lines traveling through the adipocyte network. See FIG. 18, wherein the green transfected region corresponds to the volume of tissue clamped between the plate electrodes. A closer look at a section of adipose tissue revealed many individual adipocytes. The interior of each cell is not brightly lit, because the lipid droplet does not express protein. Rather, the green fluorescent protein (GFP) is found around the edges of each cell, where protein synthesis, production, trafficking, and modification occur (see FIGS. 17, 18, and 19).

This technology was also demonstrated in rabbits (in the subcutaneous fat at the base of the neck). See FIG. 20, wherein the Oil Red O stain highlighting the lipid droplets, as well as the green ring of GFP surrounding transfected cells. Nuclei are shown in blue.

Confocal images of transfected guinea pig adipose tissue shows that the protein is produced and expressed around the entire border of the cells. The numerous, smaller cells surrounding the adipocytes do not express GFP, which is consistent with a degree of specificity for adipocytes (see FIG. 21).

Injection volume may be reduced from about 200 μl to 50 μl without impacting the size of the transfected region (see FIG. 22). Multiple injections, followed by a single EP, may be one way to increase the number of transfected cells (see FIG. 23). Decreasing voltage and increasing the number of pulses may improve GFP signal, possibly indicating more transfected cells. 80V treatments caused noticeably weaker muscle twitches compared to 200V treatments (see FIG. 24). dMAb was produced at peak levels of around 1000 ng/mL in guinea pigs following a second treatment into adipose. The first treatment was performed using un-optimized parameters (see FIG. 25).

The guinea pig receiving rapid pulses produced more dMAb than the guinea pigs receiving pulses with longer inter-pulse delays of 1 second (see FIG. 26). Jet injection appeared to distribute the DNA more uniformly throughout the tissue and transfect more cells. See FIG. 27. Enzymatic breakdown of the tissue improved fluid distribution throughout the tissue (see FIG. 28). As the number of pulses increases, electrical resistance decreases. At 25V, the current was essentially undetectable (see FIG. 30). At 100V, the muscle twitch was intense enough to cause fluctuations in the electrical readings (see FIG. 29).

Example 2. Immunogenicity. In vivo treatments were provided to five experimental groups, all of which received the same dose of DNA. For the experiment, one group was given intradermal EP to act as a positive control group. The remaining four groups were treated in the adipose layer of tissue using various combinations of high or low voltage and high or low injection volumes. Pulse voltages for the four adipose groups varied between approximately 50 V to approximately 200 V while injection parameters varied between approximately 100 microliters in a single site, to five injections of 50 microliters are each site. For each injection, plasmid was diluted to increase the volume without changing the overall DNA dose.

As illustrated in FIG. 31, the adipose groups treated with high voltage and high injection volume had a stronger and more rapid humoral immune response (i.e., end-point titer) than any other group, including the intradermal treated group. The strength of this response continued to increase through 6 weeks. Both lower voltage treatments (i.e., with high and low volume) had little to no response after 3 weeks, and had weak or no response after 6 weeks.

Both volume of the DNA injection and the voltage of the EP appear to influence the immune response in adipose tissue. The greater the volume of agent injected into the tissue corresponds with increased contact between cells and agent. Increased volume may address issues related to the administration of water-formulated DNA into adipose tissue. In addition, the higher the EP voltage, the more cells that may undergo EP. Furthermore, any tissue damage as a result of higher voltage, may aid in the induction of an immune response and associated cells.

Example 3. Materials and methods for examples 4-9. To simulate different EP modalities, two tissue models were created as 3D CAD assemblies in SolidWorks 2013 (SolidWorks Corp., Concord, Mass., USA). Both models consisted of three electrically isotropic layers: skin, adipose, and muscle. The stratum corneum was not included in these models because voltages as low as 50V will permeabilize the stratum corneum within microseconds, and its contribution to total tissue resistance then becomes negligible. The thickness of the stratum corneum is on the order of 20 μm, and very thin layers can cause artifacts in finite element analysis. To model tissue clamped between plate electrodes, a folded tissue geometry was created and two square plate electrode geometries with contact area measuring 400 $cm^2$ were placed on opposite sides of the fold (FIG. 32). To model penetrating needle electrodes within the same tissue, a flat tissue geometry was created and two 19 mm, 22-gauge needle geometries were placed into the tissue with an inter-electrode spacing of 10 mm and a penetration depth of 18 mm (FIG. 33).

The two tissue-electrode assemblies were exported to ANSYS Maxwell 2015.2 (ANSYS Software, Canonsburg, Pa., USA) for finite element analysis. Electrical conductivity values for each tissue type were based on literature values, and were assumed to be constant. Conductivity values and general tissue dimensions used in the models are listed in Table 1. An excitation voltage was applied to one electrode while the opposing electrode was assigned a voltage of zero, and cross-sections bisecting the electrodes in the x-y analysis plane were created to visualize the electric field strength.

TABLE 1

| Material | Conductivity, S/m | Thickness (folded), mm* | Thickness (flat), mm |
|---|---|---|---|
| Skin | 0.25 | 1 | 1 |
| Adipose | 0.05 | 10 | 5 |
| Muscle | 03 | 1 | 35 |
| Stainless steel | $1.1 \times 10^6$ | N/A | N/A |

*Thickness measured at the plane bisecting the electrodes

Animals. All animal studies were performed under protocols approved by an institutional animal care and use committee. Female Hartley guinea pigs were used for all in vivo studies. Treatments and blood collections were performed while animals were maintained under general anesthesia by inhaled isoflurane. Subcutaneous injections were performed into the interscapular subcutaneous fat pads (located at the scruff of the neck) using a 29-gauge insulin needle oriented parallel to the spine. For terminal studies, guinea pigs were first placed under general anesthesia and then humanely euthanized by intracardiac injection of pentobarbital.

Plasmids. Gene expression studies utilized plasmid DNA encoding green fluorescent protein (GFP). Immune studies were carried out using plasmid DNA encoding full length nucleoprotein (NP) from Influenza A (H1N1, A/Puerto Rico/8). All plasmid formulations were prepared in saline sodium citrate buffer for a final buffer concentration of 1×.

Dye injection studies. Methylene blue (Sigma-Aldrich, St. Louis, Mo., USA) was dissolved in deionized water at a concentration of 0.5 mg/mL. For single-site injections, guinea pigs were injected subcutaneously with 100 µL of methylene blue solution. For multi-site injections, five separate 50 µL subcutaneous injections were performed, spaced approximately 5 mm apart. Following injection, the entire fat pad was gripped tightly between two plate electrodes to simulate the full treatment protocol. Animals were immediately euthanized and the fat pads were imaged intact, and then dissected along the sagittal plane and imaged again to visualize dye distribution within the tissue.

General adipose-EP treatment procedure. Treatment sites were shaved and cleaned Adipose-EP treatments were performed on the subcutaneous fat pad in the interscapular region, while skin treatments were performed on the flank. For adipose treatments, tissue was pinched between two fingers to isolate the fat pad, and DNA was injected using a 29-gauge insulin needle oriented parallel to the spine. Immediately following DNA injection, two plate electrodes attached to opposing caliper jaws were coated with conductive gel and then used to pinch the tissue surrounding the injection site, and pulses were administered using the Elgen 1000 control unit (Inovio Pharmaceuticals, San Diego, Calif.). For ID-EP treatments, DNA was injected intradermally followed immediately by electroporation using the surface electroporation (SEP) device consisting of a 4×4 array of needle electrodes.

Gross imaging and histological analysis. For green fluorescent protein (GFP) studies, adipose-EP was performed with GFP plasmid, and intact fat pads were removed at predetermined time points and imaged using a FluorChem R imaging system (ProteinSimple, San Jose, Calif., USA). Fat pads were then frozen, and samples measuring approximately 10 mm×10 mm were cut from the transfected region of the fat pad and cryosectioned at a thickness of 30 microns either along the transverse plane to view the depth of transfection, or along the coronal plane to view the horizontal distribution of transfected cells. Some sections were fixed in 4% formalin, cleared in xylene, stained with either DAPI or Hoechst 3342 (Life Technologies, Carlsbad, Calif.), and coverslipped using Fluoromount (eBioscience, San Diego, Calif.). Other sections were fixed in formalin, cleared in xylene, stained with hematoxylin and eosin (H&E), and coverslipped using Permount (VWR, Radnor, Pa., USA). Sections that were H&E stained were imaged in brightfield using an Olympus BX51 microscope (Olympus, Center Valley, Pa.) equipped with a MicroPublisher 3.3 camera (QImaging, Surrey, BC, Canada). Fluorescence images were captured with a Retiga 3000 camera (QImaging, Surrey, BC, Canada). Confocal images were acquired as high resolution multi-paneled and auto-stitched z-stacks of the whole tissue using a Zeiss LSM 780 laser scanning confocal microscope (Carl Zeiss, Jena, Germany) and the images were further processed using Zen 2012 (Carl Zeiss) and IMARIS software (Bitplane, Belfast, UK).

GFP expression and cellular kinetics. Adipose-EP was performed on 14 guinea pigs, using 100 µg of a plasmid coding for GFP and EP parameters of 200V, 3 pulses, 100 ms duration, and 100 ms inter-pulse delay. As controls, two guinea pigs were treated with EP but did not receive plasmid injection, while two additional guinea pigs received the plasmid injection but were not treated with EP. Controls were sacrificed 3 days following treatments, and treated guinea pigs were sacrificed at intervals (n=2) following the treatment, ranging from 3 hours to 14 days post-treatment, as well as a long-term follow-up at day 60. Fat pads were imaged intact for GFP expression and then sectioned and stained with H&E to visualize signs of cellular infiltration at the treatment site.

Immunogenicity study. Guinea pigs were treated with 25 µg of NP DNA Four groups of guinea pigs (n=4) received adipose EP treatments as described above, and each group received either a single 100 µL DNA injection or five separate 50 µL injections, followed by a single EP treatment consisting of three 100 msec square wave pulses with a 200 msec inter-pulse delay. Guinea pigs vaccinated via ID-EP with the SEP device (n=3) served as a comparator group for this study since this method has been previously shown to transfect epidermal cells, but not subcutaneous adipocytes. The adipose-EP groups are as follows: high voltage EP with 1 injection site (HV-1), high voltage EP with 5 injection sites (HV-5), low voltage EP with 1 injection site (LV-1), and low voltage EP with 5 injection sites (LV-5). For guinea pigs receiving 5 injections, a single EP procedure was performed immediately following the final injection. The total dose of plasmid DNA was identical for all groups. The study design is illustrated in Table 2. Every three weeks for the duration of the study, 300 µL of blood was collected and plasma was stored at −20° C. until analysis. Treatments were administered at week 0, week 3, and week 6 of the study, immediately following blood collection. At week 21 of the study, all animals were boosted and 18 days later, 3 mL of blood was collected and peripheral blood mononuclear cells were separated for ELISpot analysis.

TABLE 2

| Group | n | Treatment site | Injections | Voltage, V | Total volume, µL | Total DNA dose, µg |
|---|---|---|---|---|---|---|
| HV-1 | 4 | Adipose | 1 | 200 | 100 | 25 |
| LV-1 | 4 | Adipose | 1 | 50 | 100 | 25 |
| LV-5 | 4 | Adipose | 5 | 50 | 250 | 25 |

TABLE 2-continued

| Group | n | Treatment site | Injections | Voltage, V | Total volume, µL | Total DNA dose, µg |
|---|---|---|---|---|---|---|
| HV-5 | 4 | Adipose | 5 | 200 | 250 | 25 |
| ID-EP | 3 | Skin | 1 | 25 | 50 | 25 |

ELISA Serum from vaccinated guinea pigs was analyzed using enzyme-linked immunosorbent assay (ELISA). ELISAs were performed using 96-well plates (Thermo Fisher Scientific, Waltham, Mass., USA) coated overnight with 100 µL/well of 0.3 µg/mL pNP antigen (Sino Biological, Beijing, China) in Dulbecco's phosphate buffered saline (PBS) (VWR). Plates were washed, blocked with PBS containing 3% Bovine Serum Albumin (BSA) (Sigma-Aldrich) and 0.05% Tween-20 (Sigma-Aldrich) at 150 µL/well for one hour at 37° C., and then washed again. Serum was serially diluted from 1:50 to 1:2952450 in PBS containing 1% BSA and 0.05% Tween-20 (sample dilution buffer) at 100 µL/well and incubated for two hours at 37° C. Plates were then washed, and horseradish peroxidase-conjugated goat anti-guinea pig IgG (Sigma-Aldrich) was diluted 1:10 000 with sample dilution buffer and added to each well at 100 µl/well for one hour at 37° C. Plates were washed and Tetramethylbenzidine (TMB) substrate solution (VWR) was added to each well at 100 µL/well and the color development was stopped with TMB stop reagent solution (VWR) after 6 minutes. Absorbance values at 450 nm in each well were measured using a SpectraMax PLUS 384 plate reader (Molecular Devices, Sunnyvale, Calif., USA), and the cutoff for a positive titer was calculated as described by Frey, at al., in which the mean absorbance and standard deviation of the negative controls (in this case, the pre-bleed samples) were used to calculate cutoff absorbance values. End-point titers were used for all ELISA results presented.

ELIS pot. Vaccinated guinea pigs were boosted at week 21 of the immune study, and 18 days later, 3 mL peripheral blood was drawn and collected in EDTA tubes to perform interferon gamma (IFN-γ) ELISpot, using methods previously developed in-house. The blood was diluted 1:1 with HBSS and centrifuged over Ficoll-Paque Plus (GE Healthcare Biosciences, Pittsburgh, Pa., USA). The buffy coat was harvested and resuspended at a concentration of 1×106 live cells/mL in R10 medium, and plated at a density of 1×105 cells/well on 96-well Millipore IP plates coated overnight with 5 µg/mL primary anti-IFN-γ antibody (V-E4) and blocked with 1× PBS containing 10% (w/v) sucrose and 2% (w/v) BSA In triplicate, PBMCs were incubated for 18 hours with either Concanavalin A (ConA), or one of three different NP antigen peptide pools previously found to be immunostimulatory. Following a wash to remove cells, 0.2 µg biotinylated secondary anti-IFN-γ antibody (N-G3) was added to each well and allowed to incubate for 2 hours. Wells were then washed and 100 µL BCIP/NBT detection reagent substrate was added to each well for 15 minutes. Plates were imaged using a CTL-Immunospot S6 ELISPOT plate reader, and CTL-Immunospot software was used to process and count the spots. For each animal, spot counts were normalized by subtracting the counts of unstimulated cells.

Statistical methods. To compare ELISA titer data of adipose-EP treated groups, repeated measures factorial ANOVA was performed on log-transformed titer data over all collected time points, using EP voltage, number of injection sites, and treatment week as factors. For comparisons of ELISA titer data between all treatments, data were stratified by time point and then one-way ANOVA was performed on log-transformed data using treatment group as the factor, and pairwise comparisons were made using Tukey post-hoc testing when the F-test was significant. The type II error was minimized and there was no correction for multiple comparisons in this case. ELISpot data was analyzed first within adipose-EP treated groups using factorial ANOVA, with EP voltage and number of treatment sites as factors. One-way ANOVA was performed to compare ELISA data for all treatment groups, including ID-EP. The cutoff for significance was defined as $p<0.05$, and all observations of non-significant trends and differences were accompanied by p-values.

Figure 34:
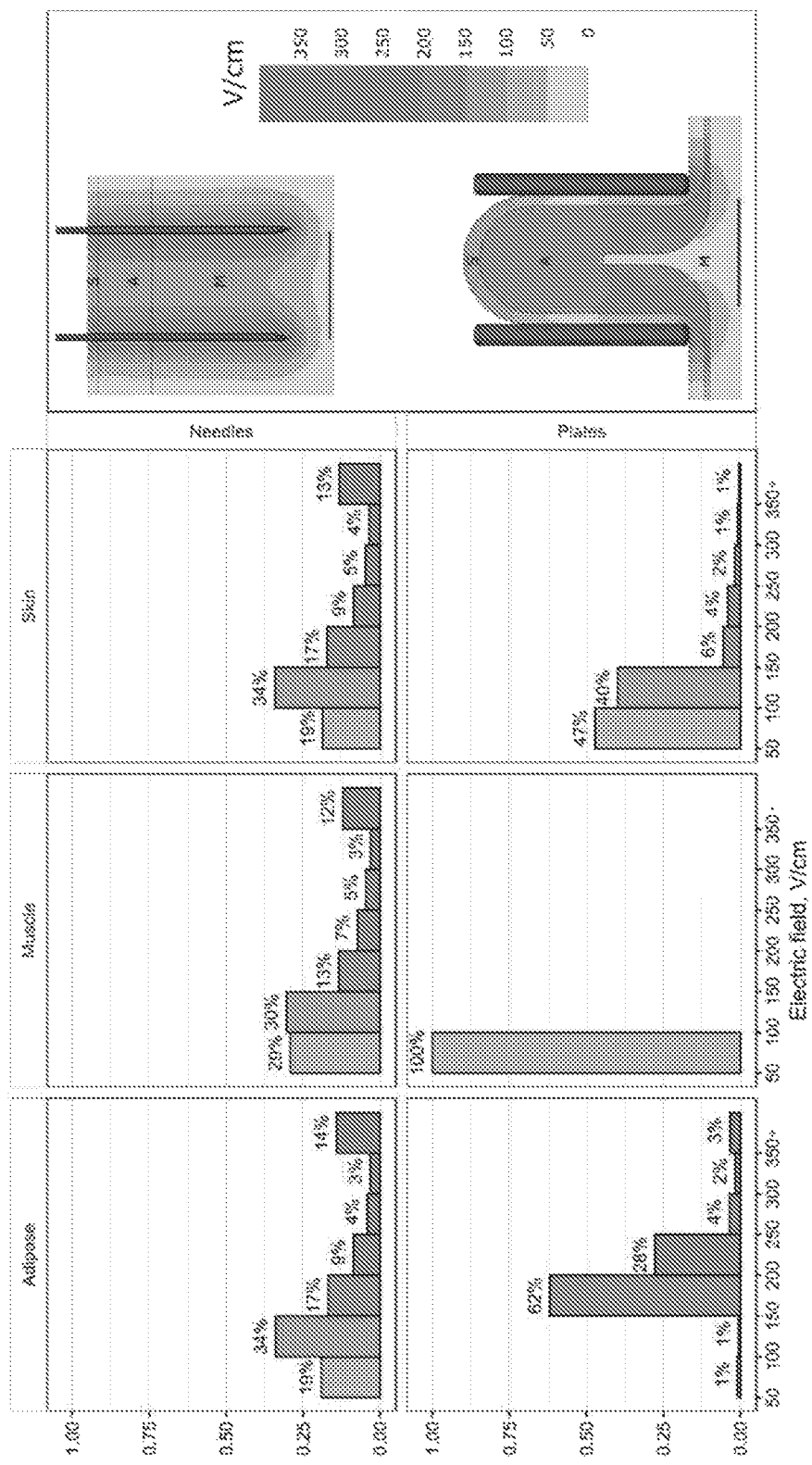
FIG. 34. Simulated electric field distribution within different tissue types for needle (top) and plate (bottom) electrode configurations using a 200V excitation voltage. The histograms (from left to right: adipose, muscle, skin) quantify the electric field distribution within each tissue type for electric fields higher than 50 V/cm. The images on the right show the electric field distributions used in the quantitative analysis, with outlines and labels for skin (S), adipose (A), and muscle (M). Each scale bar segment (white or black) is 10 mm in length, and the total scale bar length is 20 mm.

Example 4. Finite element analysis and parameter optimization. To understand the electrical properties of adipose tissue from an EP perspective, finite element analysis was carried out. This allowed the quantification of the predicted electric field distribution within each tissue type of interest (in this case, skin, muscle and adipose) which define the voltage ranges appropriate for EP in adipose tissue using the electrode design illustrated in FIG. 32. Finite element analysis in the x-y plane indicated that standard needle electrodes distributed a strong gradient of electric fields equally through skin, adipose, and muscle (FIG. 34, top), while plate electrodes generate a more uniform electric field almost exclusively within adipose tissue (FIG. 34, bottom). Needle electrodes were predicted to provide field strengths higher than 350 V/cm to 12-14% of each tissue, while approximately half of the tissue receives a field strength below 150 V/cm. Plate electrodes were predicted to produce electric fields between 150 V/cm and 350 V/cm in 95% of the treated adipose tissue, and muscle received no electric field above 100 V/cm. In these simulations, plate electrodes produced electric fields below 150 V/cm in 87% of skin.

The finite element analysis suggested that non-invasive plate electrodes actively concentrate the electric field into adipose tissue, acting conversely to needle electrodes, which provide the same electric field indiscriminately to each tissue they penetrate. Additionally, the field generated by plate electrodes is more uniform compared to needle electrodes.

The finite element model assumed constant electrical conductivity for each tissue type. Recent evidence suggests that conductivity is in fact a function of electric field strength, and therefore changes dynamically during EP. However, these dynamic models have only been validated in skin, muscle, and tumor tissue, so constant conductivity was chosen to avoid making any assumptions that might overestimate the electric field distribution. Further, it was assumed that the non-pinched fat layer located directly beneath the electrodes and limiting the current flow into underlying muscle was compressed to a thickness of 1 mm. This assumption was made in order to avoid overestimating the insulating capacity of adipose tissue, though in reality the underlying fat is likely much thicker even with the electrodes firmly in place. The results of the simulations can be considered a "worst case" scenario, and validation of a dynamic conductivity model in adipose will likely increase the predicted electric field strength throughout the fat.

Plate electrodes were chosen for subsequent experiments based on the superior calculated electric field distribution throughout adipose tissue, the minimization of electric field in other tissue types, and the noninvasive nature of the device. An optimized prototype of the plate electrode could easily be applied clinically and that the data generated in this finite element analysis could be extrapolated to the denser and thicker adipose regions in humans.

Figure 35:
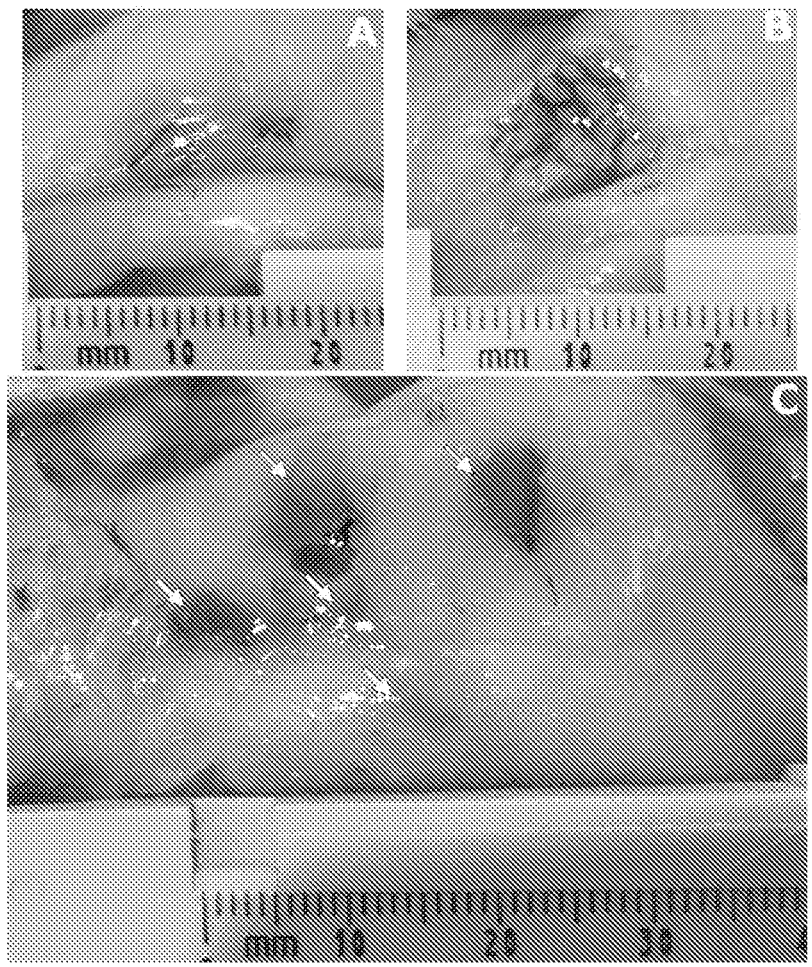
FIG. 35. Dye injection into guinea pig subcutaneous fat pad. A Intact fat pad after a single, 100 µL injection. B. Single site injection sectioned along sagittal plane to show fluid distribution within tissue. C. Intact fat pad after five 50 µL injections. Arrows indicate injection sites.

Example 5. Dye injection studies. While the fluid dynamic properties of a bolus IM or ID injection are well characterized, the distribution of a fluid within in vivo subcutaneous fat was less clear. Additionally, the physical effect on that compressing the injection site between plate electrodes might have on fluid distribution was unknown. These dynamics were investigated by dye injection studies, which were carried out to allow visualization of the distribution of injected fluid within fat. After injection and squeezing between calipers, dye was visible within intact fat pads as an elongated bolus shape (FIG. 35, top left). After dissecting the fat, dye appeared to be retained primarily within the collagenous septa dividing adipose lobes (FIG. 35, top right). The blue stain was retained within the fat pad, with little no stain present in the overlying skin or the underlying muscle. Because the dye did not appear to travel throughout the tissue after being squeezed between electrodes, the same dye analysis was performed with multiple injection sites with the objective of increasing the distribution of DNA throughout the adipose tissue. When five separate 50 µL dye injections were performed and then clamped between electrode plates, five individual dye sites remained visible, although some were more prominent than others (FIG. 35, bottom). When dissected, each individual injection sites possessed similar dye distribution within the adipose tissue, with dye concentrated along the collagenous septa.

Dye studies suggested that some injectate is in contact with the dermis, but no gene expression was observed outside of the fat pad. This observation is consistent with the finite element analysis, which suggests that electric fields of sufficient strength to cause transfection are almost exclusively generated in the adipose tissue. When multiple injections were performed, some sites were more prominent than others, which may be due to nearby injection sites merging when they are squeezed between the plate electrodes. The strongest dye staining occurred along the collagen septa dividing adipose lobes, and indeed, many transfected adipocytes were clustered around these septa. It is likely that the electric current and the DNA solution primarily travel via these collagenous septa, and adipose transfection occurs when DNA solution escapes these channels and comes into contact with nearby adipocytes prior to EP.

On a cellular level, there were ample numbers of transfected adipocytes at the injection site, easily distinguishable by their large size, characteristic globular shape and unique "ring-shaped" gene expression pattern caused by the inert lipid droplet occupying the center of each cell. The treatments appeared highly selective for adipocytes, because despite the numerous other cell types occupying space between adipocytes, GFP was only expressed around adipocytes. This is likely due to the propensity of EP to preferentially transfect larger cells at lower field strengths. Adipocytes are globular cells with very large diameter (50-100 µm), and it is possible that their shape and diameter make them more susceptible to EP than other, smaller cell types. Adipose tissue also harbors numerous immune cells, endothelial cells, stem cells, and fibroblasts, so it was somewhat surprising that there was no obvious widespread transfection of these other cell types.

Figure 36:
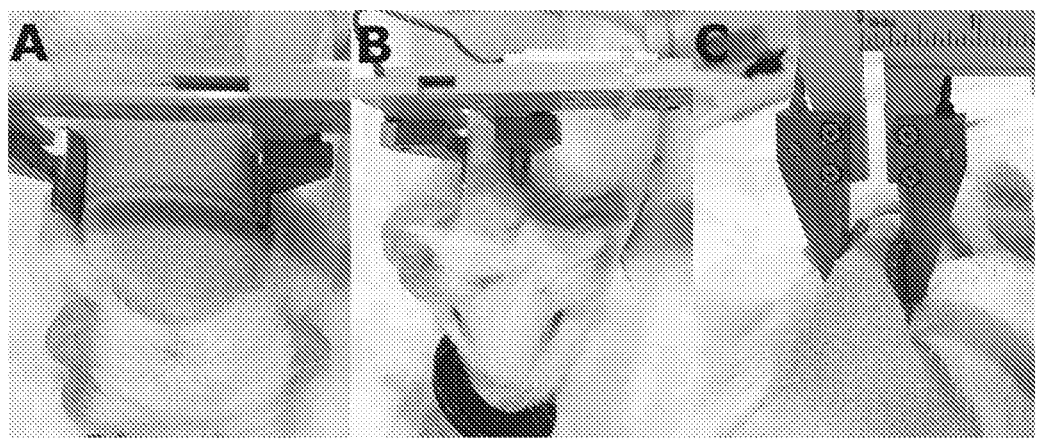
FIG. 36. Adipose-EP procedure, showing A shaved interscapular region prior to application of electrodes. B. the treatment site gripped between two noninvasive plate electrodes. C. a back view of the gripped treatment site.
Figure 37:
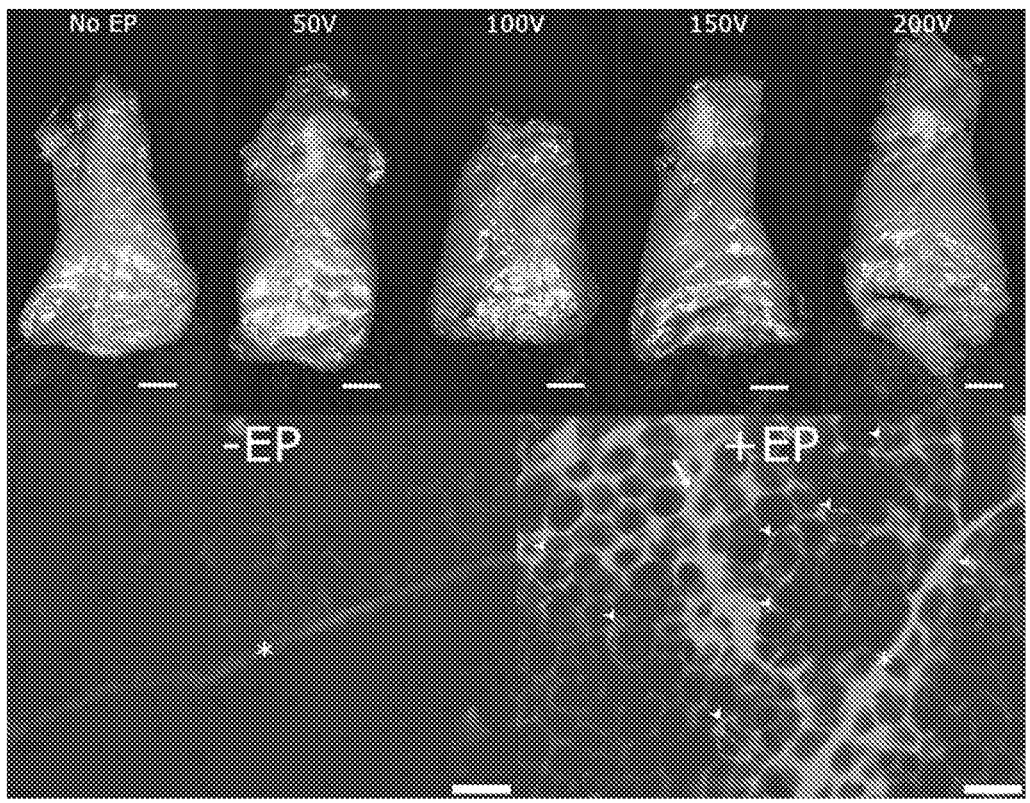
FIG. 37. Top: GFP reporter construct expression (green) distribution throughout intact guinea pig fat pads following noninvasive adipose-EP at ranging from 50V to 200V. Bottom: Comparison of fluorescent signal at treatment site for guinea pigs receiving plasmid DNA injection without EP (left) or with 200V adipose-EP (right). Markers indicate collagen septa(*), GFP-expressing adipocytes (arrowheads), and regions of high autofluorescence (arrow). Scale bars are 10 mm (top) or 100 µm (bottom).
Figure 38:
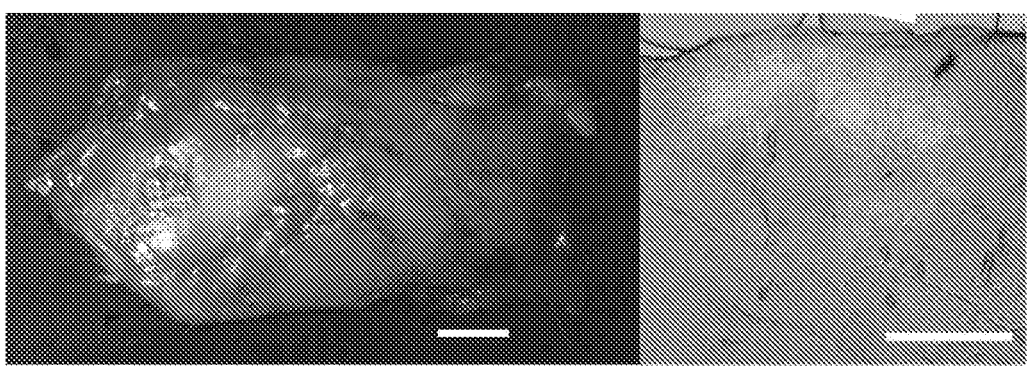
FIG. 38. An intact guinea fat pad, following adipose-EP at 200V (left) was used for further histological analysis, with the dotted line indicating the sectioning plane. Right) The section on the left was cut along the dotted line into histological sections 100 µm thick. GFP (green) is overlaid with brightfield color image of unstained tissue. Scale bars are 10 mm (left) and 1 mm (right).
Figure 39:
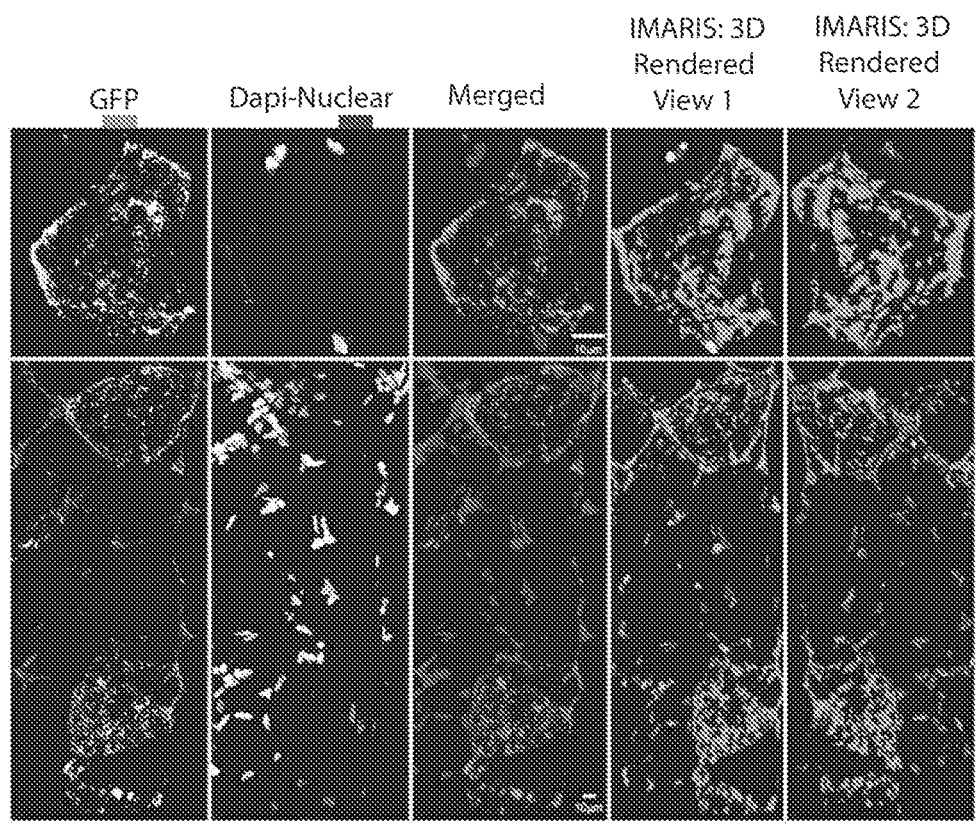
FIG. 39. Confocal image showing GFP expression (green) and nuclei (blue) in a single focal plane (middle column) and two different 3-d perspectives (right two columns).

Example 6. In vivo transfection of adipocytes. To assess to in vivo expression of a reporter construct in adipose tissue, plasmid coding for GFP was injected into guinea pig fat pads as and electroporated with voltages ranging from 50V to 200V using noninvasive plate electrodes as described in the general adipose-EP treatment procedure section in Example 3. The treatment site and EP clamping procedure is shown in FIG. 36. Three days after performing these treatments, intact fat pads were removed and imaged at the gross tissue level. GFP was expressed exclusively at the injection site within the subcutaneous fat pads in a region approximately 5-10 mm in length and 1-2 mm across, and there was no visible difference in signal area or intensity between the EP voltages tested (FIG. 37, top). No GFP expression was detected in animals receiving plasmid injection without adipose-EP. At the microscopic cellular level, adipocytes were distinguished by their large diameter (50-100 µm) and characteristic globular shape due to the lipid droplet occupying the center of the cell volume (FIG. 37, bottom). The fat pads of guinea pigs receiving adipose-EP possessed numerous GFP-expressing adipocytes that were easily distinguishable by their sharp fluorescent outline. There were regions of strong, diffuse autofluorescence located in the extracellular space between adipocytes, and the collagen septa were also prominently fluorescent. In guinea pigs receiving plasmid DNA injection without adipose-EP, there were no detectable GFP-expressing adipocytes or regions of high autofluorescence, and the collagen septa were visible, but less prominent. Further histological analysis was performed to visualize the distribution of reporter construct through the depth of the fat pad. The strongest and most abundant GFP signal was localized to adipocytes adjacent to the collagenous septa dividing the adipose lobes (FIG. 38). No GFP was detectable in the overlying skin layer. Gene expression was detectable several millimeters deep into the fat, and was generally consistent with fluid distribution observed in dye injection studies. High resolution confocal images revealed that GFP was expressed in a distinct punctate manner surrounding each transfected adipocyte (FIG. 39). GFP expression was not associated with the numerous nuclei surrounding and in between the adipocytes, which are indicative of a smaller, secondary cell population within adipose. This population includes preadipocytes, fibroblasts, and endothelial cells.

Figure 40:
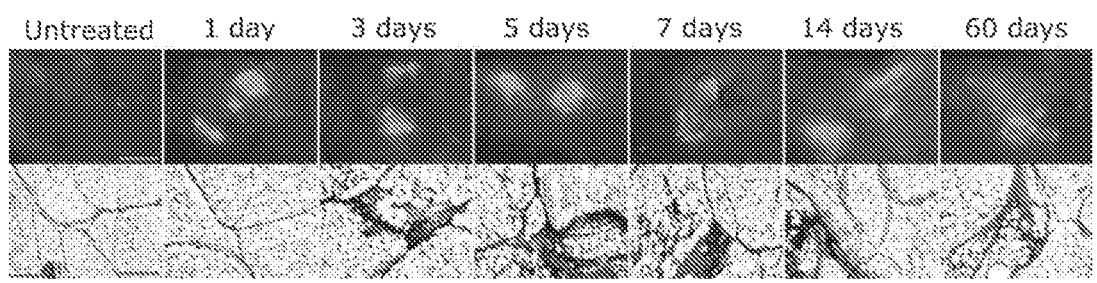
FIG. 40. Gene expression kinetics and histological changes following adipose-EP at 200V. Scale bars for GFP expression (top) are 10 mm, and scale bars for H&E stained sections (bottom) are 200 µm.

Example 7. Gene expression kinetics and histological analysis. To investigate the kinetics of reporter construct expression in an adipocyte population, a time-course study was undertaken where samples of treated fat pad were removed, sectioned and analyzed at defined time points following 200V adipose-EP with noninvasive plate electrodes. Gene expression was measurable as early as 24 hours following adipose-EP treatment, and expression was sustained throughout the 60 days monitored (FIG. 40, top). There was no clear qualitative difference in the intensity or distribution of the GFP fluorescence over the first 7 days. The signal appeared more diffuse beginning at day 14, and even weaker and more diffuse at day 60. Each distinct site of GFP expression was on the order of 10 mm in diameter. Histological changes, as observed through H&E staining of adipose sections, following adipose-EP were noticeable beginning a day 3, continued through day 14, and appeared to mostly resolve by day 60 (FIG. 40, bottom). No detectable difference in tissue physiology at 3 hours or 24 hours post-treatment was observed. At these early time points, adipocytes were well-defined, lipid storage droplets were identifiable as empty voids due to xylene clearance, and collagenous septa were visible due to darker eosin staining and numerous nuclei. Beginning at day 3 and persisting through the length of the 60 days of observation, collagenous septa at the treatment site were noticeably more prominent, likely due to the visualization of large numbers of nuclei from infiltrating cells. In regions where the collagenous septa were more prominent, the extracellular space around adipocytes became populated with higher numbers of cells as well. These histological changes were most prominent between 3 and 7 days post-treatment, and at 60 days, the infiltration into the extracellular space was mild and the cell density within the collagenous septa was still elevated, but less pronounced.

Adipose tissue was shown to be capable of rapid and sustained gene expression after a single adipose-EP treatment. There were no histological signs of cellular infiltration until 3 days post-treatment, even though gene expression was robust as early as 24 hours after treatment. However, these kinetics may differ for a highly immunogenic antigen, rather than GFP. Adipose-EP appeared to primarily transfect adipocytes, suggesting that immunogenicity is predominantly due to the antigen produced by adipocytes. Small numbers of adipocytes (20-60 cells) can be selectively transfected in vivo by directly applying EP to surgically exposed adipose tissue using forcep electrodes with approximately 0.065 $cm^2$ contact surface area. Here, a noninvasive EP technique is used to transfect large numbers of adipocytes using plate electrodes with approximately 100 times the surface area.

Figure 41:
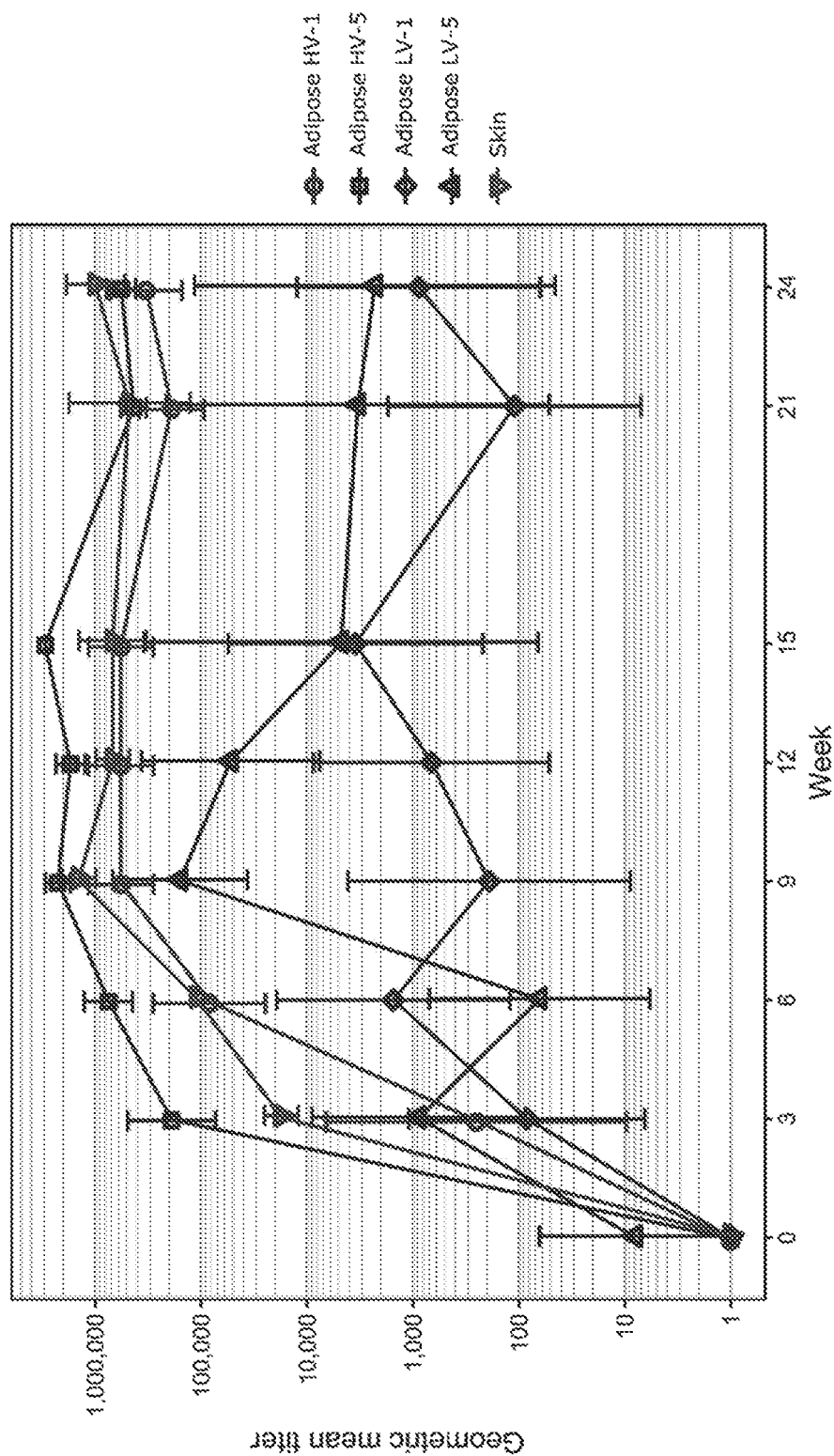
FIGS. 41 and 42. Guinea pig antibody response to adipose-EP and ID-EP vaccination with plasmid DNA encoding flu antigen. Guinea pigs were vaccinated at week 0, week 3, week 6, and week 21 with 25 µg plasmid.
Figure 42:
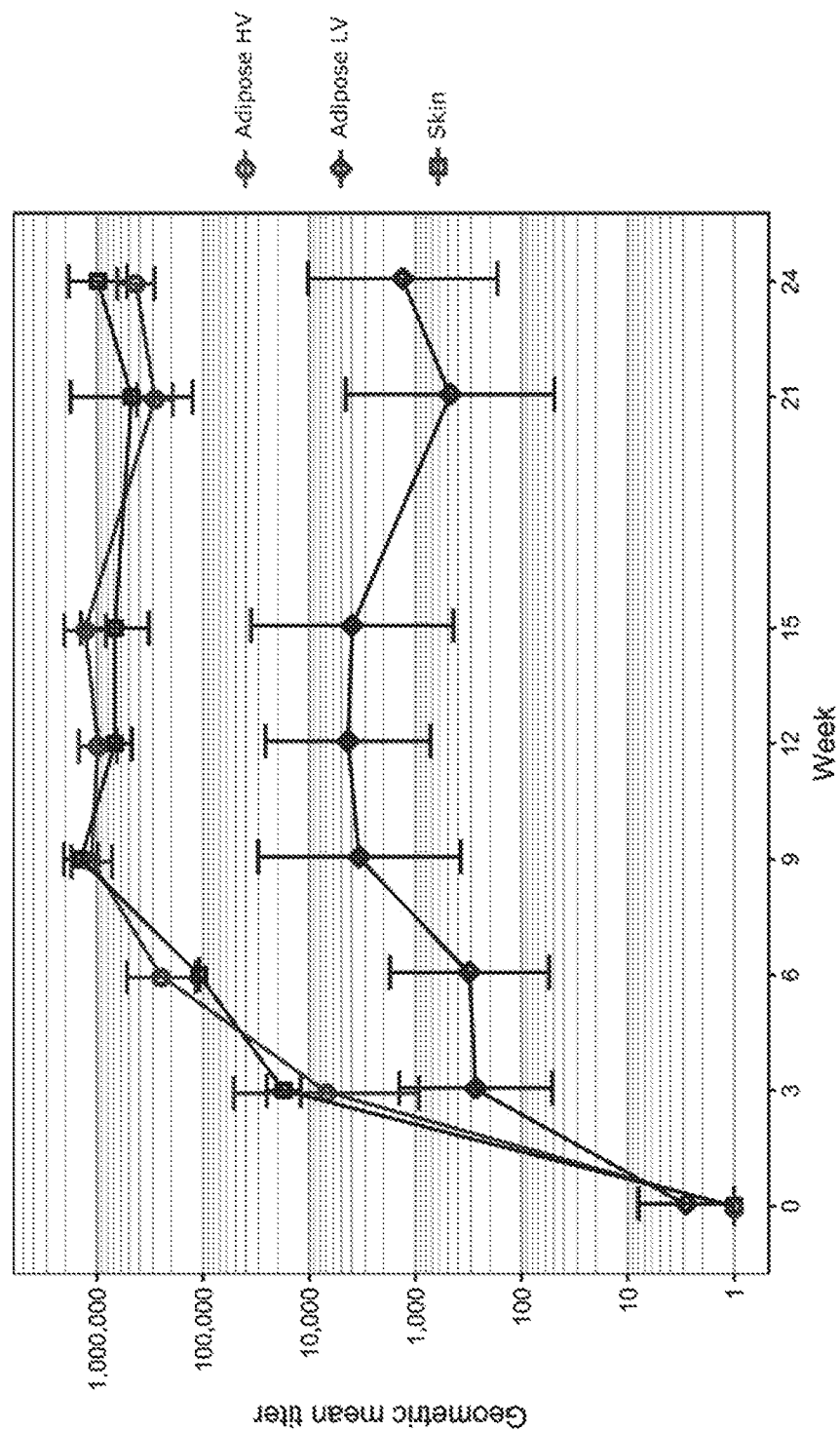

Example 8. Humoral immunogenicity. To assess the applicability of adipose tissue as a target tissue for DNA vaccination and whether an immune response can be elicited, guinea pigs were immunized with a construct expressing the influenza nucleoprotein (PR8) antigen, using adipose-EP or ID-EP as a comparison, and binding titers were measured using ELISA The adipose-EP experimental groups included high voltage EP with 1 injection site (HV-1), high voltage EP with 5 injection sites (HV-5), low voltage EP with 1 injection site (LV-1), and low voltage EP with 5 injection sites (LV-5). All guinea pigs received the same total DNA dose. HV adipose-EP and ID-EP resulted in similar antibody response kinetics, but LV adipose-EP treatments resulted in highly variable and generally lower antibody responses compared to HV adipose-EP or ID-EP (FIG. 41). Titer differences between the four different adipose-EP treatments were assessed using repeated measures factorial ANOVA There was a main effect of voltage ($p=0.0062$) and time point ($p=0.0065$), but not of number of injection sites ($p=0.16$) on titers. It appeared that multiple injection sites provides a faster onset of humoral immunity, but the interaction between number of injection sites and time was not significant ($p=0.13$). Simple main effects analysis revealed that the titer difference between HV and L V adipose-EP treatments was significant from week 6 onward ($0.0056<p<0.039$). There was no difference in titers between HV adipose-EP and ID-EP at any time point ($0.31<p<0.79$), and ID-EP provided generally higher titers than LV adipose-EP at all time points ($0.075<p<0.12$). The lack of significant difference between ID-EP and LV adipose-EP is potentially due to the number of replicates for ID-EP in this exploratory study (n=3). The delivery of a DNA vaccine, delivered into adipose tissue via EP, to induce robust humoral responses. The humoral immune response following adipose EP DNA vaccinations were shown to be both voltage- and spatial distribution-dependent, with higher voltage in particular being critical to achieve rapid, high-magnitude antibody responses. This is the first demonstration that transfected adipocytes can elicit an immune response. Strong voltage dependence was observed, despite there being no voltage-dependent differences in gene expression. The positive impact of multiple treatment sites was anticipated, since more cells are in contact with plasmid.

Figure 43:
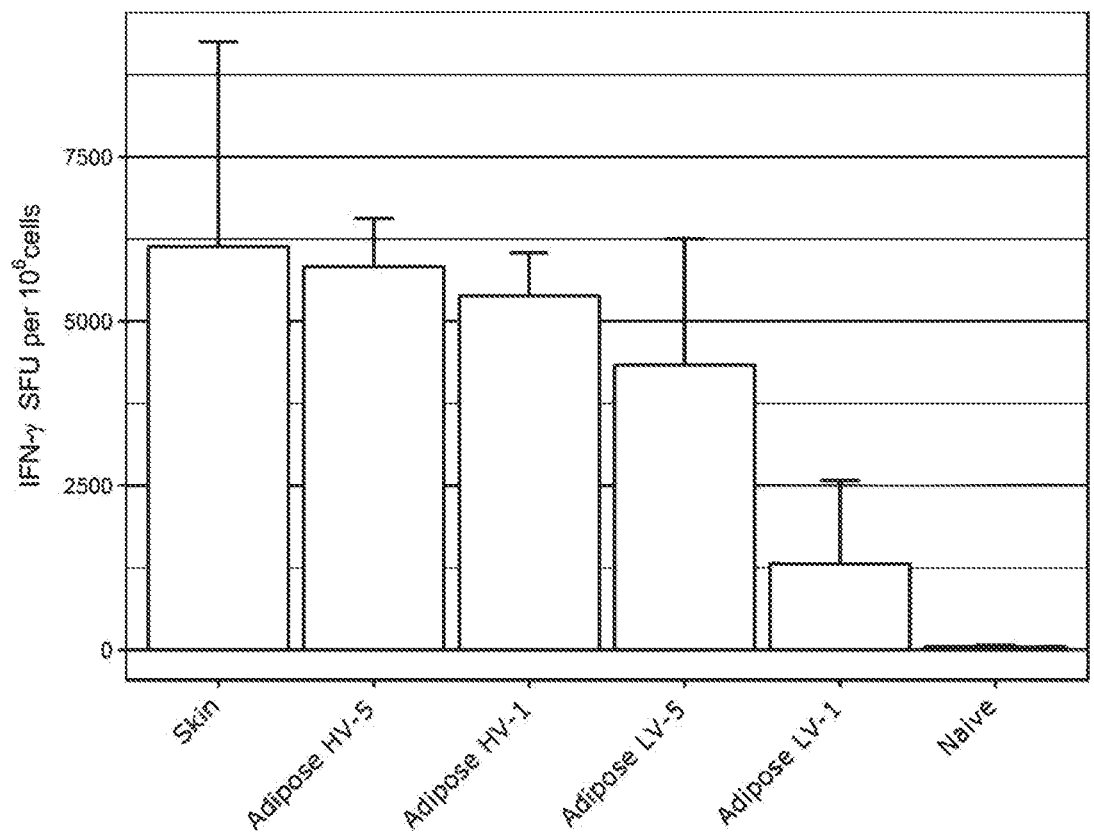
FIG. 43. Guinea pig T-cell immune response to adipose-EP and ID-EP vaccination with plasmid DNA encoding flu antigen. Guinea pigs were vaccinated at week 0, week 3, week 6, and week 21 with 25 µg plasmid, and ELISPOT was performed 18 days following the final vaccination. Results are shown for peptide pool 1. Treatments groups are divided by EP site (skin or adipose), and adipose-EP treatments are further divided by voltage (HV=200V, LV=50V) and number of plasmid injection sites (1 or 5). Data are geometric mean±standard error (n=4).

Example 9. Cellular Immunogenicity. To investigate the cellular arm of the immune response, ELISpot was performed on peripheral blood from immunized guinea pigs. HV-1 (n=3), HV-5 (n=2), and ID-EP (n=2) had fewer replicates as a result of low viable cell counts. L V-5 (n=3) had one guinea pig die due to unrelated reasons earlier in the study. All vaccinated guinea pigs produced IFN-y in response to all three peptide pools, as well as ConA. Peptide pool 1, which was the most immunogenic, was used for further analysis (FIG. 43). Spot counts appeared similar between ID-EP and HV adipose-EP groups, and appeared to trend lower for LV adipose-EP, with LV-1 in particular appearing to elicit the weakest cellular immune response. Within adipose-EP treatment groups, factorial ANOVA was revealed no significant difference in log-transformed spot counts for voltage ($p=0.15$) or number of injection sites ($p=0.26$), and there was no interaction between these two factors ($p=0.39$). One-way ANOVA comparison of all treatment groups, including ID-EP, showed no significant difference in log-transformed spot counts ($p=0.31$).

Adipose-EP was capable of producing equivalent cellular immune responses to IDEP, and though the differences between groups were not significant due to low replicates and high variability, the spot counts trended lower for those guinea pigs receiving the lowest voltage and only one treatment site. These findings support the dependence of adipose-EP immunogenicity upon both EP voltage and DNA distribution, and suggest that electroporation parameters and DNA distribution within tissue are important factors that can independently be tuned to improve immune responses.

The voltage-dependence of the antibody response has two key factors. First, higher voltages produce a larger, stronger electric field, so more cells can potentially be transfected. Transfection efficiency and immune responses have been shown to be voltage-dependent in other tissues such as skin and muscle. However, the results of the optimization studies indicated that ample transfection was occurring even at low voltages, so this is unlikely to be the only explanation. The second explanation for the voltage-dependent antibody response is that higher voltages require higher electric current, which can cause tissue damage or irritation due to resistive heating. Although the treatment sites had no external signs of damage, histological analysis showed marked cellular infiltration within adipose tissue beginning 3 days post-treatment. It has previously been suggested that EP has an adjuvant effect. Therefore, it is possible that the cellular infiltration observed is linked to the mild thermal damage caused by EP, and plays a role in the increased immune response at high voltages. Although 200V is similar to the voltages used in IM DNA EP vaccinations, the current never exceeded IA, which is also similar to IM-EP. Therefore, a similar amount of electrical energy is spread over a larger surface area (6.25 $cm^2$) compared to a typical 19-inch, 22-gauge needle (0.88 $cm^2$), so the energy density at the electrode surface should be approximately 7-fold lower in the adipose DNA EP treatment compared to IM-EP.

The mild positive effect of increasing number of DNA injection sites on immunogenicity is likely due to the increased number of cells in contact with DNA prior to EP. It was demonstrated that there is no detectable benefit to gene expression by increasing injection volume at a single site beyond 50 µL, so the same dose of DNA was distributed over 5 different sites, each receiving 50 µL injections. The fact that multi-site treatments may provide an immunogenicity benefit compared to single-site, same dose treatment, particularly at early time points, provides evidence that adipose EP DNA vaccination can directly benefit by exposing more adipocytes to DNA The results suggest that the immune response can be amplified by involving more adipocytes and providing optimal electroporation parameters. Other factors such as pulse duration, number of pulses, inter-pulse delay, and DNA concentration may all contribute to the immune response. ID-EP has been shown to be dose-sparing, but these immune data show that adipose-EP was capable of generating similarly robust immune responses at the same dose as ID-EP. Adipose tissue has the potential to accommodate much larger doses than ID-EP, similar to muscle, without the downsides of tolerability and invasiveness associated with IM-EP. The examples demonstrate that an adipose-targeted DNA vaccine is immunogenic following optimization of DNA delivery and electroporation parameters. This approach provides rapid and sustained immune responses, and does not require invasive needle electrodes. At a fixed dose of DNA, the magnitude and onset of the immune response both improve with electroporation voltage and increasing number of injection sites. Adipose-targeted EP DNA vaccination offers potential safety, tolerability, and ease-of-use advantages over IM administration and does not suffer from the dosage or cell turnover limitations of ID treatments.

What is claimed:

1. An electroporation device for use with a fold of tissue, the fold of tissue including a skin layer, an adipose layer, and a smooth muscle layer, the electroporation device including:
   a frame;
   a first arm and a second arm each extending from the frame;
   a first electrode coupled to a distal end of the first arm, the first electrode having a first contact surface defining a first perimeter; and
   a second electrode coupled to a distal end of the second arm, the second electrode having a second contact surface defining a second perimeter, wherein the first contact surface and the second contact surface face each other and define a treatment zone therebetween for communicating an electroporation signal to the fold of tissue, the first and second contact surfaces each have an electrically insulated portion and an electrically non-insulated portion, and the electrically insulated portion is located distally of the electrically non-insulated portion and extends to the distal end of the respective first and second contact surface.

2. The electroporation device of claim 1, wherein at least one of the first contact surface and the second contact surface includes a plurality of protrusions extending therefrom.

3. The electroporation device of claim 2, wherein each protrusion is substantially pyramidal in shape.

4. The electroporation device of claim 1, further comprising a hand-held applicator that comprises the frame and supports the first and second arms, the hand-held applicator including an adjustment mechanism connected to the first and second arms, wherein the adjustment mechanism is configured to allow a user to manipulate a distance between the first and second contact surfaces.

5. The electroporation device of claim 1, wherein each of the first and second electrodes includes a layer of insulating material that provides the insulated portion of the respective first and second contact surfaces.

6. The electroporation device of claim 5, further comprising first and second sheaths that define the respective layers of insulating material, wherein the first and second sheaths are attached to distal end portions of the first and second electrodes.

7. The electroporation device of claim 1, wherein the first and second electrodes are configured to grip the fold of tissue such that tissue positioned within the treatment zone includes a skin layer, an adipose layer, and a smooth muscle layer.

8. The electroporation device of claim 7, wherein the first and second electrodes are further configured such that the non-insulated portions are adjacent a top of the fold of tissue and the insulated portions contact opposite sides of the fold of tissue.

9. The electroporation device of claim 8, further comprising a third electrode having a third contact surface configured to contact the fold of tissue.

10. The electroporation device of claim 9, wherein the third electrode is located between the first and second electrodes such that the third electrode does not directly contact either the first electrode or the second electrode, and the third contact surface is configured to communicate the electroporation signal to the fold of tissue.

11. The electroporation device of claim 10, wherein the third electrode is a plate electrode configured such that the third contact surface contacts a top of the fold of tissue.

12. The electroporation device of claim 10, wherein the third electrode is a needle electrode configured to penetrate the fold of tissue and extend into the adipose layer.

13. The electroporation device of claim 1, further comprising an injection device for injecting a predetermined amount of an agent into an adipose layer of the fold of tissue.

14. The electroporation device of claim 13, wherein the injection device includes a reservoir configured to hold the predetermined amount of the agent.

15. The electroporation device of claim 14, wherein the injection device further comprises an injection needle extending from and in fluid communication with the reservoir, and the injection needle is configured to inject the predetermined amount of the agent into the adipose layer.

16. The electroporation device of claim 15, wherein the injection needle further comprises a needle electrode configured to penetrate the fold of tissue and extend into an adipose layer of the fold of tissue, the needle electrode having a third contact surface configured to communicate the electroporation signal to the fold of tissue.

17. A hand-held electroporation device, comprising:
    a frame;
    a first plate electrode coupled to the frame, the first plate electrode having a first contact surface; and
    a second plate electrode coupled to the frame, the second plate electrode having a second contact surface that faces the first contact surface, wherein the first and second contact surfaces are configured to grip a fold of tissue, the first and second contact surfaces defining a treatment zone therebetween for communicating an electroporation signal to the fold of tissue,
    wherein the first and second contact surfaces each have an electrically insulated portion and an electrically non-insulated portion, and the electrically insulated portion is located distally of the electrically non-insulated portion and extends to the distal end of the respective first and second contact surface.

18. The hand-held electroporation device of claim 17, further comprising:
- first and second arms that extend from the frame, wherein the first plate electrode is coupled to the first arm and the second plate electrode is coupled to the second arm; and
- an adjustment mechanism connected to the first and second arms, wherein the adjustment mechanism is configured to allow a user to manipulate a distance between the first and second contact surfaces.

19. The hand-held electroporation device of claim 17, wherein each of the first and second electrodes includes a layer of insulating material that provides the insulated portion of the respective first and second contact surfaces.

20. The hand-held electroporation device of claim 19, further comprising first and second sheaths that define the respective layers of insulating material, wherein the first and second sheaths are attached to distal end portions of the first and second electrodes.

21. The hand-held electroporation device of claim 17, further comprising circuitry electrically connected to the first and second plate electrodes, wherein the circuitry is electrically connectable to a signal generator for generating the electroporation signal.

* * * * *